(12) United States Patent
Chan et al.

(10) Patent No.: US 11,183,275 B1
(45) Date of Patent: Nov. 23, 2021

(54) CLINICAL DOCUMENTATION IMPROVEMENT (CDI) SMART SCORING SYSTEMS AND METHODS

(71) Applicant: Iodine Software, LLC., Austin, TX (US)

(72) Inventors: William Chan, Austin, TX (US); W. Lance Eason, Austin, TX (US); Bryan Au-Young, Austin, TX (US); Michael Kadyan, Austin, TX (US); Timothy Harper, Austin, TX (US)

(73) Assignee: IODINE SOFTWARE, LLC, Austin, TX (US)

( * ) Notice: Subject to any disclaimer, the term of this patent is extended or adjusted under 35 U.S.C. 154(b) by 1157 days.

(21) Appl. No.: 14/928,675

(22) Filed: Oct. 30, 2015

Related U.S. Application Data

(60) Provisional application No. 62/073,458, filed on Oct. 31, 2014.

(51) Int. Cl.
    *G16H 10/60* (2018.01)
    *G16H 50/20* (2018.01)

(52) U.S. Cl.
    CPC ............. *G16H 10/60* (2018.01); *G16H 50/20* (2018.01)

(58) Field of Classification Search
    CPC .............................. G16H 10/60; G16H 50/20
    See application file for complete search history.

(56) References Cited

U.S. PATENT DOCUMENTS

| | | | |
|---|---|---|---|
| 2006/0116557 A1* | 6/2006 | Moore | A61B 5/0002 600/300 |
| 2007/0276275 A1* | 11/2007 | Proctor | A61B 5/02405 600/513 |
| 2013/0297348 A1* | 11/2013 | Cardoza | G16H 40/20 705/3 |
| 2015/0039333 A1* | 2/2015 | de Traversay | G06Q 10/06395 705/2 |
| 2015/0356246 A1* | 12/2015 | D'Souza | G06Q 30/0283 705/3 |

OTHER PUBLICATIONS

Marit Helen Instefjord, et al., "Assessment of quality in psychiatric nursing documentation—a clinical audit", BMC Nursing 2014 13: 32. (Year: 2014).*

* cited by examiner

*Primary Examiner* — Evangeline Barr
(74) *Attorney, Agent, or Firm* — Sprinkle IP Law Group

(57) ABSTRACT

A patient case may be evaluated whenever new information is received or as scheduled. Evaluation may include resolving a Diagnosis-Related Group (DRG) code and determining a CDI scoring approach based at least in part on a result from the resolving. Resolving a DRG code may include determining whether a DRG code is associated with the patient case. If no DRG code is found, the system may search for an International Classification of Diseases code or ask a user to select or assign a DRG code. Using the determined CDI scoring approach, a first score may be generated and adjusted by at least one of length of stay, documentation accuracy, payer, patient location, documentation novelty, review timing, case size, or documentation sufficiency. The adjusted score may be normalized and presented to a CDI specialist, perhaps with multiple CDI scores in a sorted order.

20 Claims, 19 Drawing Sheets

| iODINE | 𝟮 Patients | ⚠ Alerts | ✉ Messages | ⓘ CDI | Admin | Reports | Support | Welcome Julie Richmond | Settings | Log Out |

| East Wing | All Patients (999) | Medicare (432) | HMO (95) | ☐ Hide Reviewed Today | 🔍 Search by Patient |

| Patient | Score | Alerts | Reviewed | Reviewed |
|---|---|---|---|---|
| Joseph Curtin ⚠ New (2)<br>Encounter #: 73901726<br>Location: 3rd Floor West Wing<br>Admitted: 01/03/14<br>Payer: Medicare<br>Attending: Dr. Jennings<br>Diagnosis: Chest Pain | 75 | Patient has BMI outside of normal range. ▲10:26 am ⓘ ✖ ⌄<br>Possible heart failure patient. IV diuretic has been ordered and the patient has elevated BNP. ▲3:15 pm ⓘ ✖ ⌄<br>15 More Alerts ⌄ | [+] Other Query<br>Mark as Reviewed | Yesterday<br>1:45pm |
| John Smith ⚠ New (2)<br>Encounter #: 27463789<br>Location: 1st Floor West Wing<br>Admitted: 01/17/14<br>Payer: Humana<br>Attending: Dr. Murphy<br>Diagnosis: Stroke | 68 | Possible heart failure patient. IV diuretic has been ordered and the patient has elevated BNP. ▲8:56 am ⓘ ✖ ⌄<br>Consult report notes midline shift or mass effect. ▲7:17 pm ⓘ ✖ ⌄<br>15 More Alerts ⌄ | [+] Other Query<br>Mark as Reviewed | Never |
| Ashley McLaughlin ⚠ New (1)<br>Encounter #: 73901726<br>Location: 2nd Floor West Wing<br>Admitted: 01/24/14<br>Payer: Medicare<br>Attending: Dr. Jones<br>Diagnosis: Pneumonia | 65 | Patient has BMI outside of normal range. ▲10:26 am ⓘ ✖ ⌄<br>Possible sepsis. Patient has elevated WBC. ▲3:15 pm ⓘ ✖ ⌄<br>15 More Alerts ⌄ | [+] Other Query<br>Mark as Reviewed | 1/9/14<br>2:38pm |
| Linda Hernandez ⚠ New (1)<br>Encounter #: 97826378<br>Location: 3rd Floor West Wing<br>Admitted: 01/26/14<br>Payer: Medicare<br>Attending: Dr. Jones<br>Diagnosis: Respiratory distress | 55 | Patient has history of heart failure. ▲11:31 am ⓘ ✖ ⌄<br>Patient has BMI outside of normal range. ▲11:56 am ⓘ ✖ ⌄<br>15 More Alerts ⌄ | [+] Other Query<br>Mark as Reviewed | 1/10/14<br>11:20am |

CLINICAL DOCUMENTATION IMPROVEMENT (CDI) SMART SCORING SYSTEMS AND METHODS

CROSS-REFERENCE TO RELATED APPLICATION(S)

This application is a conversion of, and claims a benefit of priority under 35 U.S.C. § 119 from U.S. Provisional Application No. 62/073,458, filed Oct. 31, 2014, entitled "METHOD AND SYSTEM FOR CLINICAL DOCUMENTATION IMPROVEMENT (CDI) SMART SCORING," which is fully incorporated by reference herein.

TECHNICAL FIELD

This disclosure relates generally to clinical documentation in healthcare facilities such as hospitals. More particularly, embodiments disclosed herein relate to systems, methods, and computer program products for reviewing and analyzing clinical documentation and extrapolating a numerical value representing a significance or level of potential improvement over given clinical documentation about a patient's case, useful for prioritizing patient charts for review.

BACKGROUND OF THE RELATED ART

Clinical documentation improvement (CDI) is a process typically used in healthcare facilities such as hospitals. A health information management (HIM) or CDI specialist's job is to review the information that a physician has documented about a patient in order to ensure that the documentation is accurate and complete. This process can be labor intensive because it requires the CDI specialist to understand the clinical needs of the patient and is able to find the gaps in the documentation in the patient's chart.

Currently, most CDI specialists do not have the capacity to review every patient chart and also re-review those charts on a regular (24-hour) basis to check for any physician updates that would affect the prioritization of review. Thus, a CDI specialist typically reviews patient charts in a somewhat random fashion, or they may employ relatively limited techniques for prioritizing how they review patient charts. Some examples of these methods are as follows:
(a) CDI specialists first review patient charts that have been in the hospital the longest and then work their way to the patients who were recently admitted to the hospital last. This method is inadequate because patients that only stay in the hospital for 1-2 days will likely never have their charts reviewed for clinical documentation improvement.
(b) A CDI specialist will perform reviews on brand new patients (i.e., patients whose charts have not yet been reviewed by a CDI specialist) in the mornings, and perform re-reviews (i.e., reviews on charts that have already been reviewed at least once) in the afternoons. This method is inadequate because it is focused on dedicating an equal amount of effort to initial reviews and re-reviews even though charts that need an initial review may have significantly more opportunity for clinical documentation improvement on a given day and vice-versa.
(c) Some CDI specialists use technology tools to scan documentation and flag the patient charts that should be reviewed. This method is inadequate because it flags the patient charts without differentiating which one(s) would be more important than others. Thus, every patient chart that is flagged is equally important to another patient chart that is flagged for review. Therefore, if a CDI specialist only has time to review, for example, 10 of the 12 charts that are flagged, two charts may be neglected completely at random, regardless of whether they might yield the most significant clinical documentation improvement.

Clinical documentation is at the core of every patient encounter. It must be accurate, timely, and reflect the scope of services provided. CDI can facilitate the accurate representation of a patient's clinical status that translates into coded data, which can then be translated into hospital quality report cards, physician report cards, reimbursement, public health data, and so on. As the demand for accurate and timely clinical documentation continues to increase, there is room for innovations and improvements.

SUMMARY OF THE DISCLOSURE

Embodiments provide systems, methods, and computer program products for reviewing and analyzing clinical documentation and extrapolating a numerical value representing the likelihood of improvement over given clinical documentation about a patient's case. This numerical value can be generated by a CDI scoring engine based on real time clinical information received from a hospital about the patient and can be useful for prioritizing patient charts for review by CDI specialists. When CDI specialists have a limited time to review a finite number of charts, this approach allows them to focus on the charts that have the most opportunity for clinical documentation improvement and, as a result, ensures that the documentation is accurate and corresponds to care delivered as well as the diagnoses that are being made about the patient. Another benefit of this approach is that accurate documentation can lead to accurate billing and reimbursement rates for the hospital that employs the CDI scoring engine.

In some embodiments, a method for CDI scoring may include: evaluating, responsive to a triggering event, a patient case stored in a database, the evaluating including resolving a Diagnosis-Related Group (DRG) code and determining a CDI scoring approach based at least in part on a result from the resolving. Using the determined CDI scoring approach, a first score may be generated and adjusted by one or more factors. The adjusted score may then be normalized and presented to a CDI specialist. There can be many triggering events, for instance, a change (i.e., new information) to the patient case. This change may be associated with a location of the patient, a medical condition of the patient, or an indicator created for the patient based on real time medical data from one or more hospital data sources. As another example, a scheduled event to perform case evaluation may be a triggering event.

In some embodiments, resolving a DRG code may include determining whether a final DRG code, a working DRG code, or an admitting DRG code is associated with the patient case. If no DRG code is associated with the patient case, the method may further comprise determining whether an International Classification of Diseases (ICD) code is associated with the patient case or prompting, via a user interface, a user to select or assign a DRG code for the patient case. Skilled artisans recognize that the current Ninth Revision ICD code (ICD9) can be replaced by future revisions such as ICD10, etc. without affecting the functionality of the invention disclosed herein.

In some embodiments, one or more adjustments may be applied for various purposes. These may include a length of stay (LOS) adjustment, a documentation accuracy adjustment, a payer adjustment, a patient location adjustment, a documentation novelty adjustment, a review timing adjustment, a case size adjustment, and/or a documentation sufficiency adjustment.

In some embodiments, the CDI scoring approach may utilize a DRG probability or an indicator weight. The indicator weight may be assigned a value based on subject matter expertise, or it may be computed using historical data to measure how predictive each indicator is. The computed indicator weight may be fine-tuned over time.

In some embodiments, responsive to user action received via the user interface (e.g., a CDI specialist has reviewed the patient case), the patient case may be re-evaluated. Depending upon a result from the re-evaluation, the CDI score may be updated or remain unchanged.

One embodiment comprises a system comprising at least one processor and at least one non-transitory computer-readable storage medium that stores computer instructions translatable by the at least one processor to perform a method substantially as described herein. Another embodiment comprises a computer program product having a non-transitory computer-readable storage medium that stores computer instructions translatable by a processor to perform a method substantially as described herein. Numerous other embodiments are also possible.

These, and other, aspects of the disclosure will be better appreciated and understood when considered in conjunction with the following description and the accompanying drawings. It should be understood, however, that the following description, while indicating various embodiments of the disclosure and numerous specific details thereof, is given by way of illustration and not of limitation. Many substitutions, modifications, additions and/or rearrangements may be made within the scope of the disclosure without departing from the spirit thereof, and the disclosure includes all such substitutions, modifications, additions and/or rearrangements.

BRIEF DESCRIPTION OF THE DRAWINGS

The drawings accompanying and forming part of this specification are included to depict certain aspects of the disclosure. It should be noted that the features illustrated in the drawings are not necessarily drawn to scale. A more complete understanding of the disclosure and the advantages thereof may be acquired by referring to the following description, taken in conjunction with the accompanying drawings in which like reference numbers indicate like features and wherein:

FIG. 5 depicts a diagrammatic representation of another example of a graphical user interface showing CDI scores generated by a CDI smart scoring system according to some embodiments disclosed herein.

DETAILED DESCRIPTION

The disclosure and various features and advantageous details thereof are explained more fully with reference to the exemplary, and therefore non-limiting, embodiments illustrated in the accompanying drawings and detailed in the following description. It should be understood, however, that the detailed description and the specific examples, while indicating the preferred embodiments, are given by way of illustration only and not by way of limitation. Descriptions of known programming techniques, computer software, hardware, operating platforms and protocols may be omitted so as not to unnecessarily obscure the disclosure in detail.

Various substitutions, modifications, additions and/or rearrangements within the spirit and/or scope of the underlying inventive concept will become apparent to those skilled in the art from this disclosure.

Figure 1:
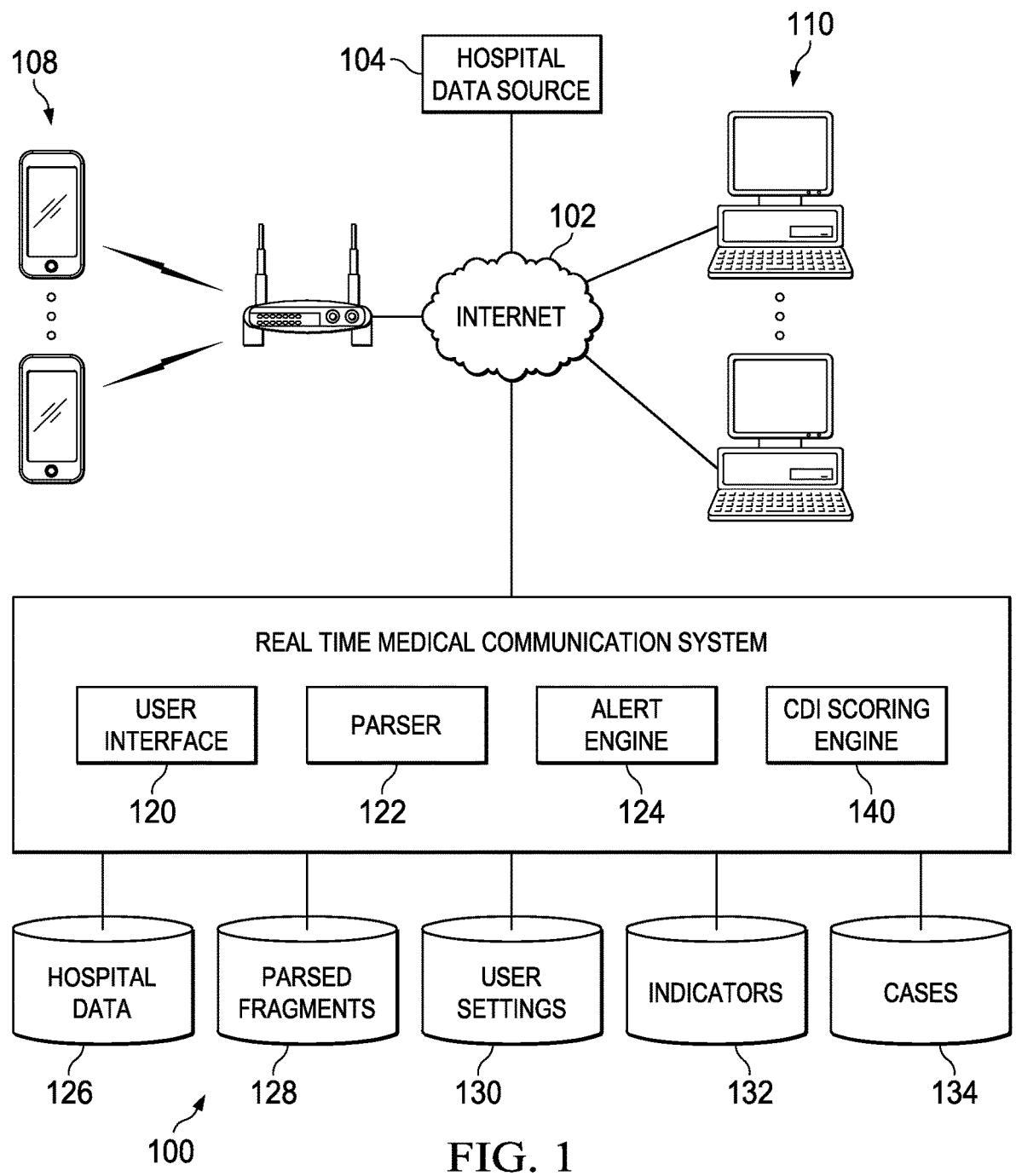
FIG. 1 depicts a diagrammatic representation of one example of a CDI smart scoring network architecture implementing embodiments disclosed herein.

FIG. 1 depicts a diagrammatic representation of one example of a CDI smart scoring network architecture implementing embodiments disclosed herein. In the example illustrated, real time medical communication system 100 is communicatively connected to hospital data source(s) 104 and various computing devices 108 . . . 110 over network 102 such as the Internet. System 100 may be embodied on a single or multiple server machine(s) and may include a plurality of system components including user interface 120, parser 122, alert engine 124, CDI scoring engine 140, and data store(s) storing hospital data 126, parsed fragments 128, user settings 130, indicators 132, and patient cases 134, etc. Database management systems such as relational database management systems (RDBMS) and programming languages such as Structured Query Language (SQL) suitable for storing, accessing, and managing data communicated to and from as well as generated and/or used by system 100 are known to those skilled in the art and thus are not further described herein.

User interface 120 may represent an interface module configured for bi-directionally communicating with computing devices 108 . . . 110 via application level protocols suitable for web based applications, mobile applications, email applications, messaging (e.g., video, audio, text, etc.) applications, and so on, and for generating appropriate graphical user interfaces suitable for displaying on computing devices 108 . . . 110. User settings 130 (e.g., a preference of a CDI specialist indicating a CDI score threshold for displaying CDI cases for review) may be received from any of computing devices 108 . . . 110 via user interface 120.

Parser 122 may be configured for receiving and processing real time medical/clinical data (e.g., hospital data 126) from hospital data source(s) 104 to generate particular fragments of interest (e.g., parsed fragments 128). Additional details on hospital data source(s) 104 and parser 122 are provided below.

Alert engine 124 may be configured for generating alerts (e.g., indicators 132) based at least in part on parsed fragments 128. Alert engine 124 may be further configured for attaching or otherwise associating an indicator thus generated to a patient's case. As an example, at the end of indicator creation, alert engine 124 may perform an "attachment" operation by creating a database record representing a particular indicator and attaching it to the patient's case in the database via, for instance, a SQL statement for a SQL relational database. Alert engine 124 is further described in detail below.

CDI scoring engine 140 may be configured for monitoring indicators 132 generated by alert engine 124 (or for monitoring or listening for events about the generation of indicators 132 or subscribing to receiving notifications about the generation of indicators 132 directly from alert engine 124). Each generated indicator 132 may include an identifier (e.g., "Visit ID") that is associated with, or otherwise references, a particular patient case 134. In one example implementation, a table "Visit" may represent the entirety of a patient's stay at a hospital. A child table related to the "Visit" table called "Alert" may have a visit ID pointing back to the Visit table that it is a part of. So, each time alert engine 124 creates an alert, a new row is added to the Alert table that is associated with the particular visit (and, hence, particular patient case 134).

CDI scoring engine 140 may be further configured for accessing patient case 134 (e.g., responsive to a triggering event), evaluating patient case 134 based on information currently available to system 100, computing a CDI score for patient case 134, and updating patient case 134 accordingly. CDI scoring engine 140 is further described in detail below.

Computing devices 108 may comprise mobile devices, such as cellular telephones, smartphones, tablet computers, personal digital assistants (PDAs), and the like, that run on various mobile operating systems such as iOS, Android, Windows Mobile, WebOS, BlackBerry OS, Palm OS, etc. Computing devices 110 may include wired computers such as desktop computers and/or wireless computers such as laptop computers that run on various operating systems such as OS X, Microsoft Windows, OpenVMS, VM, Solaris, and Linux, etc.

As a non-limiting example, each of computing devices 108 . . . 110 may include a central processing unit ("CPU"), read-only memory ("ROM"), random access memory ("RAM"), a hard drive ("HD") or any other types of non-transitory storage memory, and input/output ("I/O") device(s). The I/O devices can include a keyboard, monitor, printer, electronic pointing device (e.g., a mouse, trackball, stylus, touch pad or screen, digitizer, etc.), or the like.

As discussed above, system 100 may be embodied on a single or multiple server machine(s). Each such server machine may include CPU, ROM, RAM, HD, and I/O devices similar to those described above. Likewise, a hospital data source computer 104 may include CPU, ROM, RAM, HD, and I/O devices similar to those described above.

Although a single hospital data source 104 is shown in FIG. 1, skilled artisans appreciate that hospital data source 104 may represent a single source or multiple sources associated with a particular hospital system or healthcare facility. Furthermore, multiple hospital systems and/or healthcare facilities may be communicatively connected (via appropriate hardware, software, and network technologies) to system 100 and provide real time medical data for use by system 100, including clinical documentation generated at a hospital.

As used herein, the term hospital refers to any healthcare facility, clinic, hospital, doctor's office, etc., and the term clinical documentation refers to healthcare information that documents a patient's condition and the care given to the patient. As will be described in greater detail below, real time medical data from hospital data source 104 may be provided to system 100 via one or more feeds such as HL7 (Health Level 7) feeds. The HL7 protocol is an open source protocol promulgated by Health Level Seven International, Ann Arbor, Mich., that defines how various healthcare facilities can communicate with each other. It is noted, however, that feeds via other protocols, such as the File Transfer Protocol (FTP) or Hypertext Transport Protocol (HTTP), are also possible.

Example feeds may include admits, discharges, and transfers (ADT) feeds (i.e., procedural or administrative information relating to each patient's stay at a facility); any orders (e.g., procedures/tests ordered for a specific patient); any lab results (e.g., from blood tests, etc.); any radiology results (e.g., results of x-rays, magnetic resonant imaging (MRI), computer-assisted tomography (CAT) scans, and the like); any results of cardiology exams; any prescriptions/pharmacy orders; any actual pharmaceutical/drug administration; any billing and coding data; and so on.

In some embodiments using an HL7 feed, a stream of data is updated when an event at a particular hospital or source is updated. As discussed above, the updated raw data may be stored in a hospital data database represented by hospital data 126 in FIG. 1. Parser 122 may parse the new information, generate new parsed fragments, and store the newly generated parsed fragments. Alert engine 124 may analyze the newly generated parsed fragments, generate new indicator(s), and attach the new indicator(s) to a specific patient case. In turn, CDI scoring engine 140 may receive a notification or otherwise learn that new indicator(s) has/have been added to a specific patient case, obtain the new indicator(s) and any necessary information from the specific patient case, evaluate the patient case, generate a CDI score, and insert/update the patient case to include the CDI score thus generated.

The CDI score can be a discrete numerical value (e.g., a positive integer) representing a significance or level of improvement for clinical documentation associated with a patient in a hospital who is identified in the specific patient case. The CDI score can streamline a CDI specialist's task of determining which patient charts to review in what order, allowing them to make an informed decision as to how they could best improve the accuracy of the given clinical documentation which could, in turn, provide a positive impact on the hospital's insurance reimbursement rates, healthcare quality ranking, etc. Since CDI specialists have a finite amount of time and often cannot get to all initial reviews and re-reviews of patient charts for CDI purposes, this invention can provide them with significantly more guidance on where to spend their time in order to have the most impact when they perform CDI reviews.

For example, the system may parse newly received real time medical data concerning a patient and identify a body mass index (BMI) of the patient as a piece of information of interest (i.e., a parsed fragment). The system may determine (e.g., by consulting an indicator table storing indicator information vetted by subject matter experts) that the BMI for the patient is high and that a high BMI may be an indicator for obesity. The system may generate an indicator for obesity and attach it to the patient's case. The system may evaluate the patient's case which now includes the new indicator and determine that the current clinical documentation is missing information on obesity. Although the patient's attending physician(s) should have specified whether the patient is actually obese or overweight (if those labels apply), this documentation is commonly missed by physicians. The system can identify missing and/or inaccurate information in a patient's case and generate a CDI score such as a score of 0-100 that represents a significance or level of improvement. For example, a score of 100 may indicate that this patient's case is extremely likely to need a CDI review and the CDI review may result in a significant impact in improving the quality of the clinical documentation for this case.

By presenting a CDI specialist with a list of patient cases scored on a scale of 0-100 (e.g., via a computing device such as computing device 108 or 110), the CDI specialist can easily prioritize which patient charts to review and in what order. In some embodiments, input from a CDI specialist may also affect, both in the short term and in the long term, how the system scores patient cases for CDI reviews.

(i) Short Term Impact—once a CDI specialist has reviewed a patient's chart and has taken the necessary steps to ensuring that the clinical documentation for that patient is accurate (at the time the CDI review is complete), then, in some embodiments, the CDI score associated with the particular patient case is updated to be (or reset to) zero for the time being. This CDI score may be updated again when new information about the patient's care is received and the patient's case is re-evaluated by the system, at which time, the system may generate a new CDI score indicating that a re-review may be needed for the patient's case to further improve clinical documentation on the patient's care. Furthermore, in some embodiments, a Diagnosis-Related Group (DRG) code assigned to the patient by a CDI specialist may affect the CDI score. For example, a use-selected DRG code may have a billable/reimbursement rate that is higher than the DRG code initially assigned to the patient, which may result in the patient's case being scored higher by the system. As another example, a use-selected DRG code may indicate that a patient's reimbursement rate cannot go any higher, which may result in the patient's case being scored lower by the system.

(ii) Long Term Impact—a CDI specialist may indicate to the system (e.g., via a graphical user interface generated by user interface 120 of system 100) which of the alerts/flags resulted in actual improvement to clinical documentation. In this way, the system can learn and/or gain knowledge on what the global "success rate" of each alert/flag is relative to the CDI scoring process, and can globally adjust the weight of the alert/flag in the CDI scoring algorithm as needed.

Figure 2A:
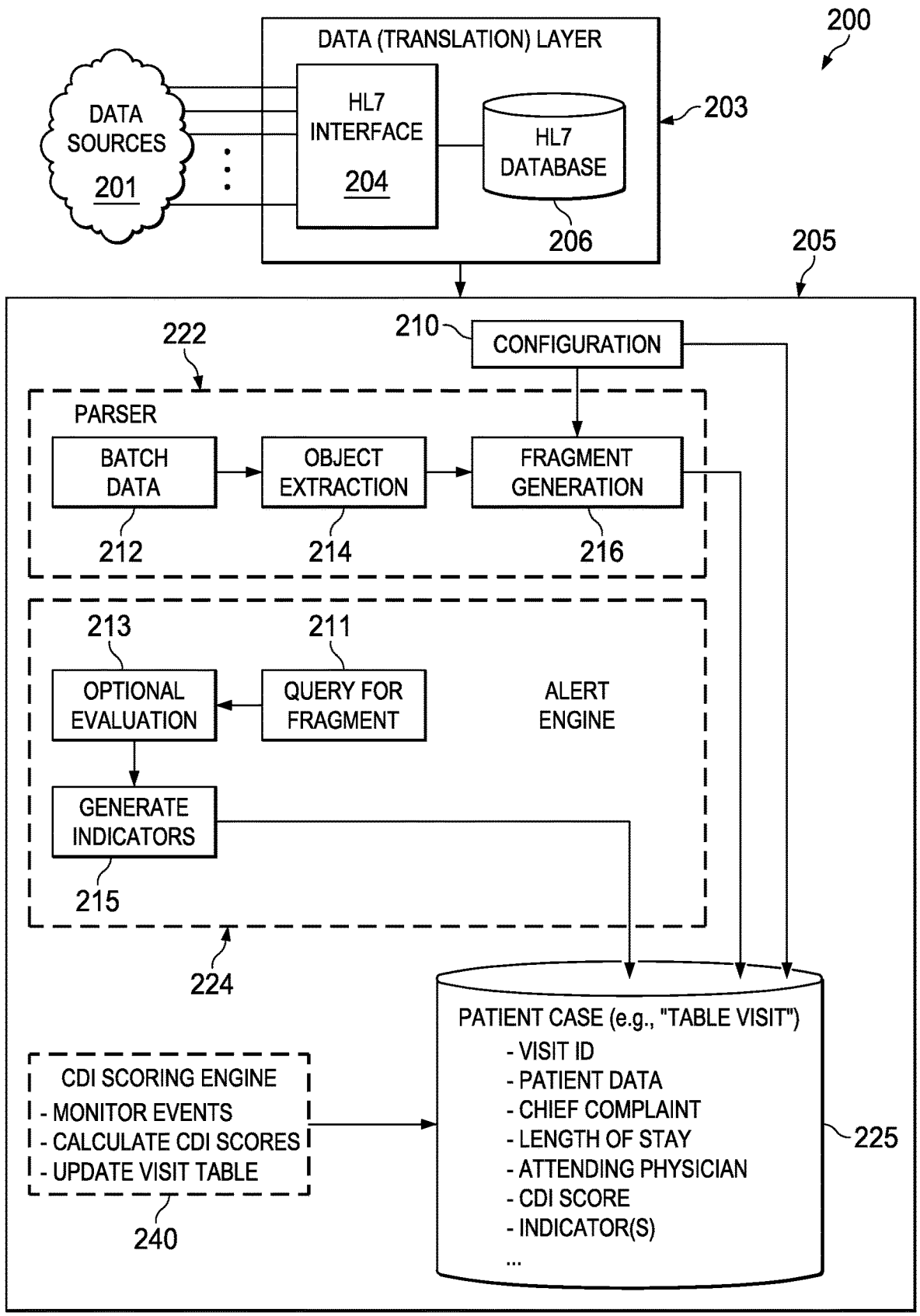
FIG. 2A depicts a diagrammatic representation of one example of a CDI smart scoring system according to some embodiments disclosed herein.

Turning now to FIG. 2A, which depicts a diagrammatic representation of one example of real time medical communication system 200 according to some embodiments disclosed herein. In the example illustrated, system 200 may include data translation layer 203 and CDI smart scoring system 205. Data translation layer 203 may include medical data processing engine or interface 204 and database 206. In some embodiments, medical data processing engine or interface 204 may be configured to conform to the HL7 standards. For the sake of brevity, medical data processing engine or interface 204 may be referred to as HL7 interface 204. In some embodiments, database 206 may be configured for storing medical data in format(s) that conform to the HL7 standards. Medical data interface 204 may receive live feeds of medical data from various hospital or care facility data sources 201. As noted above, such hospital feeds are typically maintained and updated in real time (e.g., whenever a new patient is admitted, a diagnosis is entered into the patient's chart, a procedure is performed on the patient, a drug is prescribed for the patient, a medicine is administered to the patient, a test is ordered for the patient, a result from a lab test is received, etc.).

The received medical data may be formatted as text messages (e.g., HL7 messages). HL7 interface 204 may format the received HL7 messages into rows and columns and store same in database 206.

An exemplary HL7 message is shown below. In particular, shown below is a sample HL7 message representing the results of a complete blood count (CBC) lab procedure:
MSH|^~\&|LAB|IODINE|||201306121531||ORU^R01|ID12345|P|2.3|||||
PID|1|MRN12345|ACCT98765|1221|SMITH^BOB||19850608|M|||12345
MAIN ST^AUSTIN^TX^^78701|||||||ACCT98765|123-45-6789|||||||
PV1|1|I|FACILITY.1|||DRID12345^JOHNSON^SALLY||NONE^None||||||N||REF||N|||||||||||||||CMC||FACILITY.1|||201306101110||||||
ORC|||||||||||||||||OBR|1|ORDER123^LAB|ORDER123^LAB^ALTORDER5678|CBC^LABCBC|||201306111212|||||||201306111244||DRID12345^JOHNSON^SALLY
||||||LA B|F||^^^^R|||||||
OBX|1|ST|WBC^WBC^L|8.7|K/uL|3.6-10.8|N||F|||201306111244||

OBX|2|ST|RBC^LAB RBC^L|1|4.83|M/uL|4.2-5.4|N||A^S|F|||201306111244||
OBX|3|ST|HGB^Hemoglobin^L|1|13.6|g/dL|12.0-16.0|N||A^S|F|||201306111244||
OBX|4|ST|HCT^Hematocrit^L|1|40.7|%|37-47|N||A^S|F|||201306111244||
OBX|5|ST|PLT^Platelet Count^L|1|390|K/uL|150-400|N||A^S|F|||201306111244||
OBX|6|ST|MPV^MPV^L|1|10.2|fL|7.4-10.4|N||A^S|F|||201306111244||
OBX|7|ST|GRP^Gran % (Auto)^L|1|74.7|%|42-72|H||A^S|F|||201306111244||
OBX|8|ST|LYP^Lymph % (Auto)^L|1|18.9|%|20.5-51.1|L||A^S|F|||201306111244||
OBX|9|ST|MIDP^Mid Range % (Auto)^L|1|6.4|%||N||A^S|F|||201306111244||
OBX|10|ST|GRA^Gran # (Auto)^L|1|6.5|K/uL|1.8-7.7|N||AS|F|||201306111244||
OBX|11|ST|LYA^Lymph # (Auto)^L|1|1.6|K/uL|1.0-4.8|N||A^S|F|||201306111244||
OBX|12|ST|MIDA^Mid Range #(Auto)^L|1|0.6|K/uL||N||A^S|F|||201306111244

The first line—the MSH segment—indicates that this is a result (as indicated by "ORU-R01").

The 2nd line—the PID (patient identifier) segment—provides identifying information about the patient. In this example, the patient's name is Bob Smith; he lives at 12345 Main St.; his medical record number is MRN12345; and his account (case) number is ACCT98765.

The 3rd line—the PV1 (patient visit) segment—provides status information about the patient's current visit. In this example, the message segment indicates that he is an inpatient who was admitted on 6/10/2013 at 11:10 am.

The 4th line—the OBR segment—provides information about the order that was previously placed that caused this lab procedure to be performed. In this example, the message segment indicates that Dr. Sally Johnson ordered the procedure with id "CBC" and named "LAB CBC" at 12:12 pm on 6/11/2013.

Each of the remaining lines contains a single result. For example:
OBX|1|ST|WBC^WBC^L|8.7|K/uL|3.6-10.8|N||F|||201306110124||
OBX=indicates that this line contains a result
1=indicates that this is the first result line returned for the order
ST=indicates that the result contains a simple string value.
WBC^WBC LAB^L=indicates that the result is a "WBC LAB" result with an ID of "WBC".
8.7=This is the actual numerical result
K/uL=These are the units of measure for the result
3.6-10.8=This is the reference range for this particular result
N=This is where abnormality flags would be. N indicates "normal".
F=Final status
201306111244=Observation occurred at 12:44 pm on 6/11/2013

Processing of this exemplary HL7 message by HL7 interface 204 results in the generation of structured data (e.g., a plurality of rows) which are then added to a table designated for storing lab results (e.g., a "LabResult" table) in HL7 database 206.

In some embodiments, CDI smart scoring system 205 is configured for processing the "translated" data (translated from text messages to structured data) stored in HL7 database 206 and may include parser 222, alert engine 224, CDI scoring engine 240, and database 225. Parser 222 may be configured for processing data stored in HL7 database 206 and generating parsed fragments that can be used by alert engine 224. In some embodiments, processing by parser 222 may be done by first batching medical data received in real time and translated at data translation layer 203 per source and/or data type. More specifically, in some embodiments, parser 222 may include batch data processing module 212 configured for batch processing predetermined amounts of data from each hospital feed source 201 (e.g., by type of feed, such as ADT, Orders, etc.), one source at a time. In some embodiments, each type of data is associated with a table and the tables are processed one at a time, as discussed above.

Each batch of data is passed to entity extraction module 214, which identifies whether there is an entity, object, or concept (collectively referred to herein as "entity") of interest or a modification to an existing entity. An entity of interest may represent a new patient, case, caregiver (e.g., an attending physician, a nurse assigned to the patient, a nurse assigned to the floor where the patient is located, etc.), diagnosis, procedure, order, drug, lab result, etc. For example, if an entity of interest indicates that a new attending physician has appeared in the medical data received about a particular patient, entity extraction module 214 may extract the entity of interest and create a new database entry for storing information about the attending physician.

Returning to the example given above, depending on configuration information 210 pertaining to the "LabResult" table (which can be defined or specified by an administrator or authorized user of system 205), when entity extraction module 214 processes batch data (e.g., rows of data) associated with the "LabResult" table (which is a table associated with a particular data type), it would extract or update (if necessary) an entity for the attending physician referenced, and could create one or more fragments from the various OBX lines. The entity created or updated in this example would be an "attending physician". The system may:

search an attending physician in database 225 with an identifier "DRID12345";
create an entry for this attending physician if "DRID12345" does not exist; set the first name to "SALLY" and the last name to "JOHNSON"; and save the entry with information for the new attending physician in database 225.

In some embodiments, no other entities would be created from these rows of the "LabResult" table in HL7 database 206 because patient-related information is not (and does not need to be) extracted from lab results. In processing an ADT (Admit/Discharge/Transfer) message, however, a number of different entities (e.g., patient, case, caregiver, etc.) may be created and/or updated.

The extracted entities may be stored in database 225 for use by fragment generation module 216. In some embodiments, fragment generation module 216 may also process the batch data to identify and extract pieces of information (e.g., fragments of data) that may be of interest. For example, events of interest may be extracted from the batch data (e.g., based on configuration information 210 that identify or specify such events) and stored in database 225. Fragments may be of different types and, as discussed further below, may be used to generate alerts. An alert may be generated from one or more fragments. Other methods of alert generation may also be possible. In some embodiments, configuration information 210 may include fragment definitions that can be used by fragment generation module 216.

For example, two fragment definitions may be defined (e.g., in XML) as follows:

```
<bean id="wbcFD"
class="com.iodinesoftware.rta.alertsengine.rules.fragment.
GenericNumericLabResultFD">
    <property name="observationIdsForMatch" value=
"WBC"/>
    <property name="msgFieldMap">
      <map>
        <entry key="units" value="str2"/>
      </map>
    </property>
</bean>
<bean id="hgbFD"
class="com.iodinesoftware.rta.alertsengine.rules.fragment.
GenericNumericLabResultFD">
    <property name="observationIdsForMatch" value=
"HGB,ZZHGB"/>
    <property name="deactivationPolicy"
ref="ageBasedFragmentDeactivationPolicy3"/>
    <property name="lowerThreshold" value="12"/>
    <property name="upperThreshold" value="16"/>
    <property name="invert" value="true"/>
    <property name="msgFieldMap">
      <map>
        <entry key="units" value="str2"/>
      </map>
    </property>
</bean>
```

The first fragment definition (which is associated with the bean ID "wbcFD") configures an instance of the generic fragment definition "GenericNumericLabResultFD" to search for WBC results. Using the configured "observationIdsForMatch" parameter, this fragment definition specifies what to look for in the rows from the LabResult table in HL7 database 206 (e.g., the orderServiceId field has a value of "WBC"). If a row of data from HL7 database 206 matches a fragment definition, then a fragment is created and a number of fields are set on the fragment. In this example, much of the data set on the fragment is controlled by the semantics of GenericNumericLabResultFD. In some embodiments, the system may automatically set the patient ID, case ID, ordering physician ID, observation ID, order ID, order name, observation value, observed results date, and message control ID. From the associated configuration for this fragment definition, the system may also set the units.

Referring back to the HL7 example above, this fragment definition would match the LabResult row created from the first OBX segment. Specifically, this would create a fragment with the following fields:
Fragment.patientId="MRN12345" (patient ID)
Fragment.caseId="ACCT98765" (case ID)
Fragment.str1="8 . . . 7" (observation value as a string)
Fragment.str2="K/uL" (units for observation)
Fragment.str3="CBC" (ID of ordered procedure)
Fragment.str4="LAB CBC" (name of ordered procedure)
Fragment.str5="ORDER123" (order number)
Fragment.str6="N" (abnormality flag)
Fragment.str7="1" (first result)
Fragment.cgId1="DRID12345" (ID of ordering physician)
Fragment.fp1=8.7 (numerical value for observation)
Fragment.date1=6/11/2013 12:12 pm (order time/date)
Fragment.date2=6/11/2013 12:44 pm (observation time/date)

This fragment may be stored in database 225 for use by other components of system 205 such as alert engine 224.

Similarly, the second fragment definition may be used to match any result rows with an observation ID of either "HGB" or "ZZHGB". In this example, it would create a fragment populated with the data contained in the third row created from the HL7 message above.

In general, any number (e.g., hundreds) of fragments of different types may be defined. For example:
wbcFD—captures white blood cell count
hgbFD—captures hemoglobin values
ctResultFD—captures the results of a Cat Scan report
microFD—captures culture and sensitivity results from a culture
transferFD—captures a patient transfer event
bunCreatResultFD—captures the numerical value of either a BUN (Blood Urea Nitrogen) or Creatinine result
directAdmitFD—captures that a direct admit event happened
dischargePlanningConsutOrderedFD—captures that a discharge planning consult has been ordered In some embodiments, configuration information 210 may further include rules for configuring and generating alerts. In some embodiments, an alert may be associated with a fragment definition and a configuration rule. Such rules may be dynamically configured by users of system 205 on an ongoing basis. Alternatively or additionally, rules may be set by a healthcare facility, such as a hospital. In some embodiments, configuration information 210 may store definitions of events that are of interest to a particular user. Depending upon fragment definitions and configuration rules, there can be many different types of alerts.

In some embodiments, alert engine 224 may include query module 211 configured for querying database 225 for cases (e.g., a state of a visit, with or without being triggered by a new fragment being generated) or fragments (e.g., for each alert rule in configuration information 210) or combinations thereof. Optionally, evaluation module 213 may perform one or more predetermined evaluations on the fragments to determine if particular criteria have been met. Results from evaluation module 213 may trigger generation of alerts. For each alert, one or more routing filters may be applied. In some embodiments, an alert may be assigned to one or more users who are members or subscribers of system 205. In some embodiments, alerts may be stored or discarded and in others, may be maintained for presentation to a user after the user is logged into system 205—only a notification about an alert may be sent to the user. The notification can include login information (e.g., a link) for the user to access and view the particular alert.

As an example, an alert may be generated for a particular patient if an unnecessary echocardiogram is performed (or ordered to be performed). In such an example, three fragments may be defined: Match Any Data from an Order Table of an Echocardiogram recently ordered; existence of a recent result of an echocardiogram; and only heart failure patients with an elevated BNP result.

```
<bean id="bnpResultFD"
class="com.iodinesoftware.rta.Alertsengine.rules.fragment.
GenericLabResultFD">
    <property name="name" value="bnpResultFD" />
    <property name="observationIdsForMatch" value="BNP"
/>
    <property name="handleLargeResultStrings"
value="false" />
    <property name="deactivationPolicy"
ref="ageBasedFragmentDeactivationPolicy5" />
</bean>
```

```
<bean id="elevatedBnpFilter"
class="com.iodinesoftware.customers.cov.rta.Alertsengine.Query
Filter">
        <property name="query">
            <value><! [CDATA[
                SELECT f FROM Fragment f WHERE
f.fragmentDefName = 'bnpResultFD' AND f.fp1 >= 100 AND
f.caseId = :caseId
            ]]></value>
        </property>
    </bean>
    <bean id="echoOrderFD"
class="com.iodinesoftware.rta.Alertsengine.rules.fragment.
GenericOrderFD">
        <property name="name" value="echoOrderFD" />
        <property name="orderServiceIdsForMatch"
value="ECHO" />
        <property name="deactivationPolicy"
ref="ageBasedFragmentDeactivationPolicy4" />
    </bean>
    <bean id="echoResultFD"
class="com.iodinesoftware.rta.Alertsengine.rules.fragment.
GenericLabResultFD">
        <property name="name" value="echoResultFD" />
        <property name="orderServiceIdsForMatch"
value="ECHO" />
        <property name="handleLargeResultStrings"
value="true" />
        <property name="deactivationPolicy"
ref="ageBasedFragmentDeactivationPolicy4" />
    </bean>
    <bean id="recentEchoAR"
class="com.iodinesoftware.rta.Alertsengine.rules.Alert.Generic
QueryAR">
        <property name="name" value="recentEchoAR" />
        <property name="admissionStatusFilter"
value="INPATIENT,OBSERVATION" />
        <property name="frequency" value="NO_LIMIT" />
        <property name="query" >
            <value><! [CDATA[
                SELECT f1, f2 FROM Fragment f1, Fragment
f2
                WHERE
                    f1.active = true
                    AND f1.fragmentDefName =
'echoOrderFD'
                    AND f2.fragmentDefName =
'echoResultFD'
                    AND f2.str7 = '1'
                    AND f1.patientId = f2.patientId
                    AND f1.date1 > f2.date2
                    AND timestampdiff(DAY, f2.date2,
f1.date1) <= 182
            ]]></value>
        </property>
        <property name="additionalFragmentsQuery">
            <value><! [CDATA[
                SELECT f FROM Fragment f
                WHERE
                    f.fragmentDefName =
'echoResultFD' AND f.patientId = :patientId
                    AND f.date2 = (SELECT
max(f2.date2) FROM Fragment f2 WHERE f2.fragmentDefName =
'echoResultFD' AND f2.patientId = :patientId)
                    ORDER BY f.long5
            ]]></value>
        </property>
```

Once the fragments are defined, one or more filters may be provided. Such filters may define, for example, an age of patient or other parameters associated therewith.

```
<property name="filters"
    <list>
        <bean
class="com.iodinesoftware.rta.Alertsengine.impl.PatientAgeAlert-
Filter" >
            <property name="minAge" value="18" />
        </bean>
        <bean
class="com.iodinesoftware.rta.Alertsengine.impl.CaseAttrAlert-
Filter" >
            <property name="attrMatches">
                <map>
                    <entry key="facility"
value="*,!CPH" />
                </map>
            </property>
        </bean>
        <bean
class="com.iodinesoftware.rta.Alertsengine.impl.CompositeAlert
Filter" >
            <property name="filterExpression"
value="elevatedBnpFilter|historyOfChfFilter" />
        </bean>
    </list>
</property>
<property name="signatureFields" value="str1" /> <! -
- order # for current order -->
<property name="routingRules">
    <list>
        <!-- Default rule -->
        <bean
class="com.iodinesoftware.rta.Alertsengine.rules.Alert.Base-
AlertRoutingRule">
            <property name="selectionPolicy">
                <bean
class="com.iodinesoftware.rta.policies.impl.NamedUserAlert-
TargetSelectionPolicy">
                    <property name="username"
value="sysadmin" /> <!-- TODO: Update to real recipient! -->
                </bean>
            </property>
        </bean>
    </list>
</property>
```

An alert may then be generated from the above example fragments and filters:

```
<property name="title" value="Echocardiogram within the past 6
months" />
<property name="shortDescription" value="Echo within
past 6 months" />
<property name="fullDescription">
    <value><! [CDATA[
        <div class="Alert-desc-title">
            Echocardiogram within the past 6
months
        </div>
        <div class="Alert-desc-desc">
            Receive a Notification when an
Echocardiogram has been ordered, the patient had one within
the past 6 months, and the patient either has a history of CHF
and/or has a BNP result > 100.
        </div>
        <div class="Alert-desc-recpt">
            Recipient: TBD
        </div>
    ]]></value>
</property>
```

An example of alert engine 224 is provided in U.S. patent application Ser. No. 13/921,647, filed Jun. 19, 2013, entitled "REAL-TIME EVENT COMMUNICATION AND MANAGEMENT SYSTEM, METHOD AND COMPUTER PROGRAM PRODUCT," which is fully incorporated by reference herein.

As noted above, there can be many different types of alerts, depending upon fragment definitions and applicable configuration rules. In some embodiments, a particular type of alerts (e.g., base DRG alerts) may be useful as indicators for the purpose of generating CDI scores. Referring to FIG. 2A, indicators thus generated (e.g., by indicators generation module 215 of alert engine 224) may be stored in database 225 for use by CDI scoring engine 240.

In some embodiments, CDI scoring engine 240 may implement a CDI smart scoring algorithm described below.

Objectives of the CDI smart scoring algorithm may include prioritizing patient cases that have the highest potential for generating additional reimbursement or documenting additional severity and provide quality answers with limited information and, as more information is provided, improved answers. To quantify these objectives, a possible improvement may be dollar weighted and adjusted by probability. As an example, a 20% chance to find an additional $10,000 is a bigger opportunity ($2,000) than a 90% chance to find an additional $1000 ($900).

Characteristics of the CDI smart scoring algorithm may, in some cases, include balancing between magnitude of potential change and proximity to discharge—a patient with a smaller opportunity but close to discharge may be a higher priority for review than a larger opportunity that was just admitted; factoring in the value of reviewing the case while it is still active before the patient leaves the facility and before the doctor's focus shifts to new cases; favoring new information—a patient with an overall higher value case but for whom all the information was present at the last review will score lower than a patient with a smaller opportunity but for whom some of the information is new (e.g., new alerts); understanding that re-reviewing a case with no new information is less likely to discover an opportunity than reviewing a case with new information; and overestimating rather than underestimating an opportunity (because clinical documentation as given tends to be imperfect). For example, if received medical data contains evidence of a kidney infection (with a relative weight of 0.78) and septicemia (with a relative weight of 1.10), septicemia is used as the basis. As another example, if data for historical performance in documenting BMI as a comorbidity is missing or insufficient, the CDI smart scoring algorithm may err on the side of assuming it is undocumented (missing) rather than assuming it is documented.

Factors considered by the CDI smart scoring algorithm when evaluating the opportunity a particular patient case represents may include:
 What is wrong with the patient
 What secondary conditions (comorbidities and complications) are exacerbating the patient's primary condition
 How good is the attending physician for the case (or are physicians in general) at correctly documenting the conditions associated with this patient
 Is the patient in a hospital location such as the intensive care unit (ICU) or telemetry that hints at greater severity for that patient
 Who is the payer for the patient and how much do they pay relative to payers for other patient cases
 How much has happened to the patient since the last review
 Is the patient close to discharge (because it would be easier to correct the documentation prior to discharge)

An example CDI model implementing the CDI smart scoring algorithm will now be described.

In this non-limiting example, the opportunity that a CDI score measures is the chance to improve the clinical documentation of a patient case such that the case moves from one Medicare Severity-Diagnosis Related Group (MS-DRG) to a higher reimbursing (more severe) MS-DRG, reflecting the actual level of care provided to the patient. As such, the baseline unit of measure used here is the same one that the MS-DRGs themselves are measured in—the relative weight. The CDI model considers the difference between a baseline and a target for each patient. The baseline represents what the relative weight for a patient case would be without any documentation improvements (no review at all), while the target represents what the relative weight actually should be based on the evidence the system has about the patient case. The difference between the baseline and the target (adjusted by probability and other factors discussed below) is referred to as the opportunity for that case.

Initial Scoring for a New Patient.

Since an opportunity is based on the difference between a baseline and a target for a patient, in some cases, the target for a new patient may need to be set before anything about their case is known. While the system does not know how this particular case is going to unfold, the system knows statistically the nature of cases for a population in which the new patient is in. As such, a starting target can be the mean relative weight as measured historically for the population. Hospitals already calculate the mean relative weights, known as the case mix index (CMI), of their patient populations. CMI is a relative value assigned to a diagnosis-related group of patients in a medical care environment. The CMI value is used in determining the allocation of resources to care for and/or treat the patients in the group. Patients are classified into groups having the same condition (based on main and secondary diagnosis, procedures, age, etc.), complexity (comorbidity) and needs. These groups are known as Diagnosis Related Groups (DRGs), or Resource Use Groups (RUGs).

Each DRG has a relative average value assigned to it that indicates the amount of resources required to treat patients in the group, as compared to all the other diagnosis-related groups within the system. The relative average value assigned to each group is its CMI. The CMI of a hospital reflects the diversity, clinical complexity and the needs for resources in the population of all the patients in the hospital and represents an average weight across all the Medicare cases in the hospital.

If for some reason the CMI for a patient cannot be obtained, the system may fall back to using the national mean which Medicare has already normalized to be the relative weight 1.

If the statistical target for a new case is the mean relative weight of the population, the statistical baseline can be calculated by taking the target minus the average adjustment found by CDI specialists for cases they reviewed. If the target cannot be determined, the system may use an assigned value as to the expected average adjustment found by CDI per case and adjust based on actual data as historical data is accrued.

Example: Acme Hospital

| | |
|---|---|
| CMI: | 1.37 |
| Medicare Base Rate: | $10,000 |
| Average CDI Adjustment: | $2,000 |
| Average CDI Relative Weight Adj.: | ($2000/$10000)* 1.37 = .274 |
| CMI without CDI Adj.: | 1.37 − .274 = 1.096 |

Example: Patient Jane Smith

| | |
|---|---|
| Chief complaint: | ? |
| LOS: | ? |
| Attending: | ? |
| Payer: | ? |
| Alerts: | (none) |
| Baseline: | 1.096 |
| Target: | 1.37 |
| Unadjusted Opportunity: | .274 |

Factoring in Medical Conditions Associated with the Patient.

Relative weights for severity/reimbursement vary widely based on the base DRG identified for the patient. As discussed above, the system may identify and examine/analyze numerous pieces of information that hint at what is wrong with the patient, including chief complaint (free text), the patient's history, diagnoses of the patient (can either be free text or coded values), procedures that have been performed for the patient, medications prescribed, lab result values, etc. The CDI scoring engine (e.g., CDI scoring engine 240) does not need to analyze each of those pieces of information separately; instead, it can leverage outputs from the alert engine (e.g., alert engine 224) which is capable of evaluating and generating base DRG alerts (which, in some embodiments, may be referred to as indicators generated by indicators generation module 215 of alert engine 224). Base DRG alerts identify aspects of the patient case that point towards specific DRGs or families of potential DRGs. Base DRG alerts focus on identifying DRGs that are more severe or more resource intensive to care for, as well as base DRGs that have a wide range of reimbursement based on accurate documentation of the nature and severity of the problem (wide ranges between the base level and the complications or comorbidities (CC) or major complications or comorbidities (MCC) level).

When a base DRG alert (i.e., an indicator) is generated, the difference between the relative weight for the base level of that DRG (without CC/MCC) and the baseline average of 1 is added to the target. Note that this may actually reduce the target if what is identified is a low severity condition. If multiple base DRG alerts are generated, the maximum of all base DRG alert adjustments may be added.

Example: Patient Jane Smith, with an Indicator Reflecting Procedure Code "06180J9"

| | |
|---|---|
| Chief complaint: | cirrhosis w/ internal bleeding |
| LOS: | ? |
| Attending: | ? |
| Payer: | ? |
| Procedures: | 06180J9 Bypass Portal Vein to Right Renal Vein with Synthetic Substitute, Open Approach |
| Medications: | Lactulose |
| Alerts: | Liver procedure (base DRG: pancreas, liver and shunt procedures, relative weight 1.828) |
| Baseline: | 1.096 |
| Target: | 1.37 + (1.828 − 1) = 2.198 |
| Unadjusted Opportunity: | 1.102 |

Working DRGs

In some embodiments, users can enter or otherwise assign a working DRG code in a patient's case. These working DRGs can be used to identify diagnoses related to the patient and the patient's anticipated reimbursement level at the current state of the patient's visit. When a CDI specialist has entered a working DRG code, the system may use the base DRG for that working DRG code as the authoritative value.

Factoring in Secondary Conditions

Comorbidity alerts (which reflect comorbidity and complications) identify aspects of a patient case that increase the severity of that case. In some embodiments, comorbidity alerts can be evaluated in different ways based on whether or not one or more base DRG alerts have been generated for the patient. If base DRG alerts are present, the comorbidity condition is compared against each DRG to identify whether the condition is considered a CC or MCC for the base DRG in question (based on the MS-DRG grouper data). If it is the actual CC or MCC adjustment for that base DRG, then the appropriate weight is added to the target. In the event of multiple base DRG alerts, each is weighted with comorbidities individually and the max adjustment (most severe) is used as the target adjustment.

Additionally, if a base DRG alert is triggered, the system may pull and examine the associated documentation to uncover any evidence that the proper documentation terms were already used. If the relevant terms are found, then the weight of the corresponding DRG alert is reduced accordingly.

For patients without an identified base DRG alert, a population average adjustment is used. This population average is the relative weight contributed to each base DRG (if any) by this comorbidity (based on MS-DRG grouper date) scaled by the percentage of cases represented by that base DRG (from CMS statistics).

Example: Patient Jane Smith, with an Indicator Reflecting a Secondary Condition

| | |
|---|---|
| Chief complaint: | cirrhosis w/ internal bleeding |
| LOS: | ? |
| Attending: | ? |
| Payer: | ? |
| Procedures: | 06180J9 Bypass Portal Vein to Right Renal Vein with Synthetic Substitute, Open Approach |
| Medications: | Lactulose |
| Alerts: | Liver procedure (base DRG: pancreas, liver and shunt procedures, relative weight 1.828) Malnutrition (MCC, pancreas, liver and shunt procedures w/ MCC has relative weight 5.575) |
| Baseline: | 1.096 |
| Target: | 2.198 + (5.572 − 1.828) = 5.94 |
| Unadjusted Opportunity: | 4.844 |

Factoring in Historical Documentation Performance

Figure 2B:
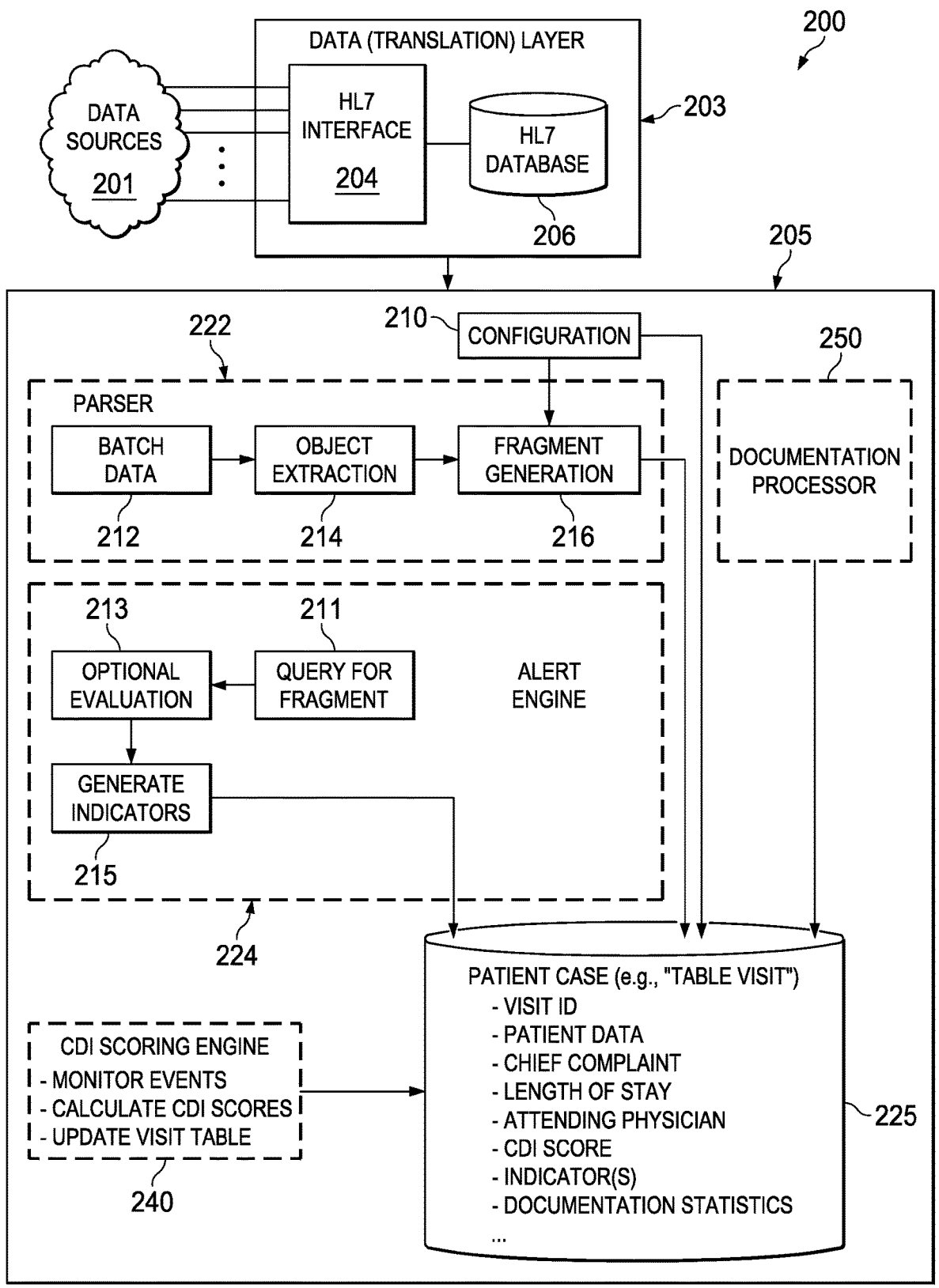
FIG. 2B depicts a diagrammatic representation of another example of a CDI smart scoring system according to some embodiments disclosed herein.
Figure 2C:
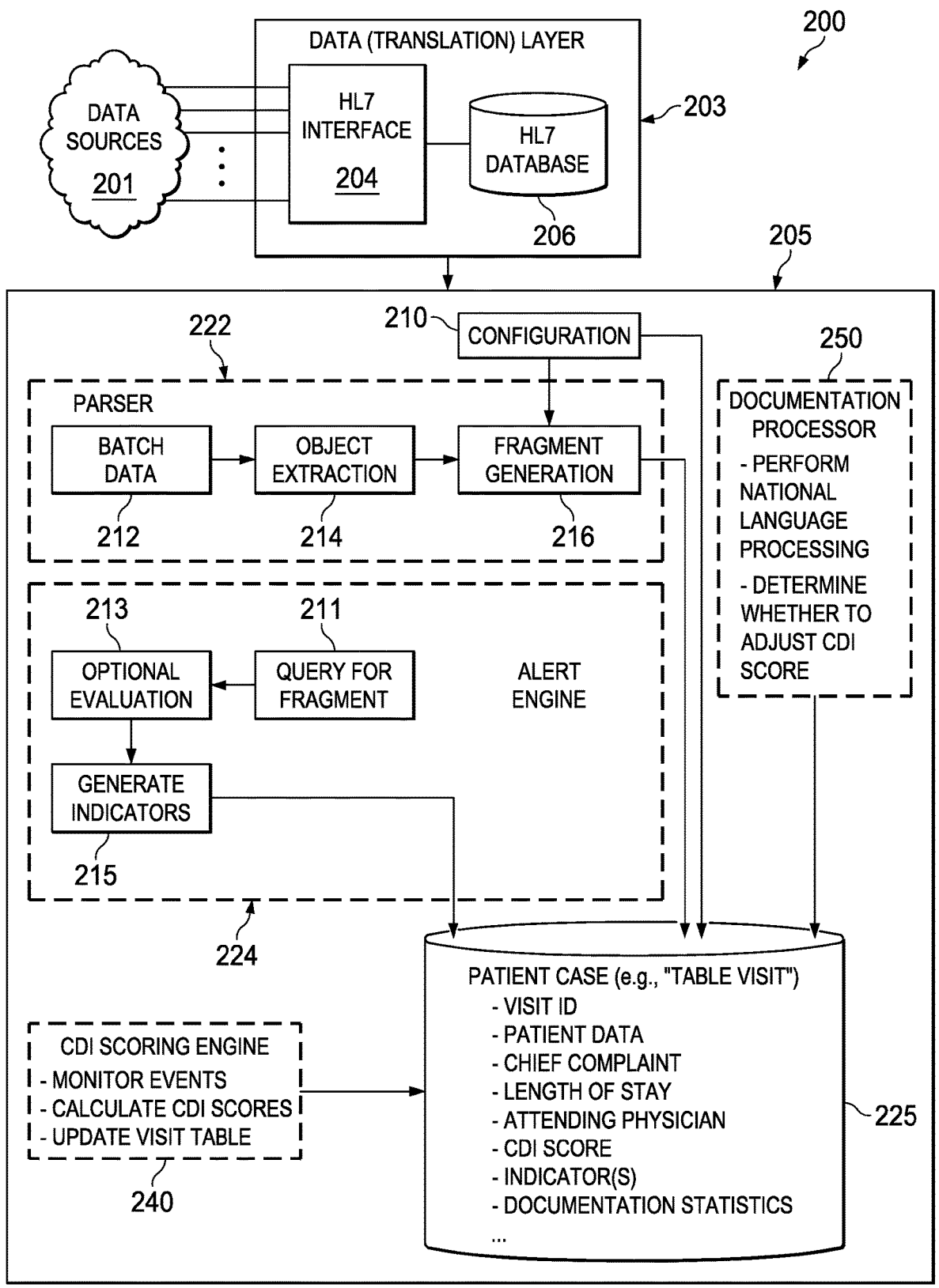
FIG. 2C depicts a diagrammatic representation of yet another example of a CDI smart scoring system according to some embodiments disclosed herein.

After factoring in adjustments for the patient's health condition, the system has the magnitude of the potential adjustment in relative weight terms. In some embodiments, historical performance numbers may be used to adjust for the probability that the documentation is actually inadequately specific. Referring to FIG. 2B, in some embodiments, system 205 may further include documentation processor 250 configured for analyzing incoming documentation and determining statistical information such as the historical accuracy rate associated with a hospital or physician. In some embodiments, as illustrated in FIG. 2C, documentation processor 250 may be further configured for various analyses such as natural language processing that may then be used to identify particular concepts that may be relevant to certain medical conditions in a case and that may affect how the case may be scored.

On an alert by alert basis, the relative weight adjustments may be discounted based on the historical accuracy rate. For instance, if an alert indicates the patient has a BMI comorbidity with a relative weight adjustment of 0.6, but historical data shows that the hospital has 100% accuracy in documenting BMI. Accordingly, there is no actual opportunity for improvement based on a CDI review and the system therefore applies a 100% discount the value of that alert to 0. If, on the other hand, BMI is historically inaccurately documented in 40% of cases for that hospital, then the relative weight is adjusted to 0.6*0.4=0.24.

In some embodiments, two dimensions of historical performance may be considered: the accuracy rate of documenting the specific condition indicated by the alert and the overall accuracy rate of the physician. If we have values for both, the lower of the two accuracy rates is used.

In the absence of historical data, an initial default accuracy rate of 0% is used as a starting point. For patients where base DRG data is present, each potential base DRG is scored individually with a maximum comorbidity adjustment across all comorbidities of 100% (i.e. if there's a 10% accuracy rate for BMI and a 20% accuracy rate for Malnutrition and both are MCC's for the base DRG that does not add up to a 170% chance of finding an MCC adjustment for the case).

Example: Acme Hospital, with Relevant Accuracy Rates

| Base DRG Alert (Indicator) | Accuracy Rate |
|---|---|
| Liver procedure | 80% |
| Comorbidity Alert | Accuracy Rate |
| Malnutrition | 30% |
| Attending Physician | Accuracy Rate |
| Dr. Smith | 50% |

Example: Patient Jane Smith, Adjusted to Reflect Historical Accuracy Rates

| | |
|---|---|
| Chief complaint: | cirrhosis w/ internal bleeding |
| LOS: | ? |
| Attending: | Dr. Smith |
| Payer: | ? |
| Procedures: | 06180J9 Bypass Portal Vein to Right Renal Vein with Synthetic Substitute, Open Approach |
| Medications: | Lactulose |
| Alerts: | Liver procedure (base DRG: pancreas, liver and shunt procedures, relative weight 1.828) Malnutrition (MCC, pancreas, liver and shunt procedures w/ MCC has relative weight 5.575) |
| Baseline: | 1.096 |
| Target: | 5.94 |
| Unadjusted Opportunity: | 4.844 |
| Probability Adjusted Target: | 1.37 + ((1.828 − 1) * (1 − min(.8, .5))) + ((5.572 − 1.828) * (1 − min(.3, .5))) = 1.37 + .414 + 2.6208 = 4.405 |
| Probability Adjusted Opportunity: | 3.309 |

Factoring in Payer Differences

A payer represents an entity that reimburses the hospital for a patient's care and is a multiplier based on reimbursement. For example, if Medicare reimburses $1000 and the payer reimburses $1100 for the same DRG, then that payer's adjustment factor is 1.1. If they reimburse $900 for the same DRG, then that payer's adjustment factor is 0.9.

For non-DRG payers, the default way to model non-DRG payers would be with an adjustment factor of 0. There may be some value in assigning a nominal value even to non-DRG payers, though non-DRG payers frequently still weigh the DRG in deciding whether claims are reasonable or not. Thus, there's the same incentive to make sure the highest value/most severe cases are documented correctly.

Example: Acme Hospital, with a Payer Adjustment Factor

| Payer | Adjustment Factor |
|---|---|
| Medicare | 1 |
| Allied Health | .9 |

Example: Patient Jane Smith, Adjusted to Reflect a Particular Payer

| | |
|---|---|
| Chief complaint: | cirrhosis w/ internal bleeding |
| LOS: | ? |
| Attending: | Dr. Smith |
| Payer: | Allied Health |
| Procedures: | 06180J9 Bypass Portal Vein to Right Renal Vein with Synthetic Substitute, Open Approach |
| Medications: | Lactulose |
| Alerts: | Liver procedure (base DRG: pancreas, liver and shunt procedures, relative weight 1.828) Malnutrition (MCC, pancreas, liver and shunt procedures w/ MCC has relative weight 5.575) |
| Baseline: | 1.096 |
| Target: | 5.94 |
| Unadjusted Opportunity: | 4.844 |
| Probability Adjusted Target: | 4.405 |
| Probability Adjusted Opportunity: | 3.309 |
| Payer Adjusted Opportunity: | 3.309 * .9 = 2.978 |

Reimbursement vs. Severity

Of all the adjustments the system may apply when analyzing a CDI opportunity, the payer adjustment is the only one that does not equally apply to severity as it does to reimbursement. If both severity and reimbursement are used as adjustment factors, a weighting factor between the two systems of measurement may be used. In the example above, the opportunity in terms of severity is 3.309 and the opportunity in terms of reimbursement is 2.978. If reimbursement is twice as important to the hospital as accurate severity documentation (the weight for reimbursement is 0.667), the system may be configured to consider the payer adjusted opportunity to instead be (2.978*0.667)+(3.309*0.333)=3.088.

This adjustment can be especially important if the severity factor is to be emphasized even across non-DRG payers where the payer adjusted opportunity would be low to none.

Factoring in Special Hospital Locations

Certain locations in the hospital such as the ICU and telemetry intrinsically may raise the probability that the case is a more severe case. If the system has the hospital's CMI by location, the system can calculate an adjustment factor for these locations; otherwise, the system may use assigned values for the severity adjustment (or not adjust by location at all). As with the payer factor, the severity factor is a multiplier applied to the adjusted opportunity.

Example: Acme Hospital, with a Severity Adjustment Factor

| Location | Severity Adjustment Factor |
|---|---|
| ICU | 1.3 |

Example: Patient Jane Smith, Adjusted to Reflect the Severity

| | |
|---|---|
| Chief complaint: | cirrhosis w/ internal bleeding |
| LOS: | ? |
| Attending: | Dr. Smith |
| Location: | ICU |
| Payer: | Allied Health |
| Procedures: | 06180J9 Bypass Portal Vein to Right Renal Vein with Synthetic Substitute, Open Approach |
| Medications: | Lactulose |
| Alerts: | Liver procedure (base DRG: pancreas, liver and shunt procedures, relative weight 1.828) Malnutrition (MCC, pancreas, liver and shunt procedures w/ MCC has relative weight 5.575) |
| Baseline: | 1.096 |
| Target: | 5.94 |
| Unadjusted Opportunity: | 4.844 |
| Probability Adjusted Opportunity: | 3.309 |
| Payer Adjusted Opportunity: | 2.978 |
| Location Adjusted Opportunity: | 2.978 * 1.3 = 3.871 |

Factoring in the Novelty of the Information

In some embodiments, the system may consider whether the information is new since the last review (if any). A case where nothing has changed since the last review is less interesting than a case where much of the opportunity comes from new information. This can be factored in by comparing the score as it stands now (with the new information) to the score as it stood at the last review (or the baseline if no previous review has occurred) to determine the delta corresponding to new information. A weighting factor can be used to balance between overall opportunity size and the new opportunity delta, with a default weight of 80% towards new data. In some cases, this may effectively back out some of the contribution of previously reviewed data to the opportunity size.

Example: Acme Hospital, with a Novelty Factor

| | |
|---|---|
| new data priority: | 80% |

Example: Patient Jane Smith, Adjusted to Reflect the Novelty Factor

At the time the patient was last reviewed the Liver Procedure alert has already been generated, but Malnutrition has not yet been identified. This is illustrated below:

| | |
|---|---|
| Chief complaint: | cirrhosis w/ internal bleeding |
| LOS: | ? |
| Attending: | Dr. Smith |
| Location: | ICU |
| Payer: | Allied Health |
| Procedures: | 06180J9 Bypass Portal Vein to Right Renal Vein with Synthetic Substitute, Open Approach |
| Medications: | Lactulose |
| Alerts: | existing: Liver procedure (base DRG: pancreas, liver and shunt procedures, relative weight 1.828) new: Malnutrition (MCC, pancreas, liver and shunt procedures w/ MCC has relative weight 5.575) |
| Baseline: | 1.096 |
| Target: | 5.94 |
| Unadjusted Opportunity: | 4.844 |
| Probability Adjusted Opportunity: | 3.309 |
| Payer Adjusted Opportunity: | 2.978 |
| Location Adjusted Opportunity: | 3.871 |
| Location Adjusted Opportunity (last review): | .805 |
| Novelty Adjusted Opportunity: | ((3.871 − .805) * .8) + (3.871 * (1 − .8)) = 3.227 |

Factoring in Temporal Proximity to Discharge

In some embodiments, the CDI scores may be generated in a way to incentivize reviewing patients prior to discharge. This can be done by linearly discounting the opportunity so far computed the farther the case is from the expected discharge date based on the expected length of stay (LOS). A minimum LOS is defined before which the score will be discounted to 0. Once reaching the expected LOS the opportunity is no longer discounted. For patients where no base DRG alerts have been generated, the mean LOS of the entire population can be used (which can default to 5 based on Medicare statistics). If one or more base DRG alerts have been generated, the system may use the minimum GMLOS for the base DRGs pointed to by those base DRG alerts adjusted by their CC/MCC levels rounded down to the nearest full day.

In some embodiments, three variables may control this LOS discount function:
1. The minimum length of stay—controls an initial window before which the opportunity is fully discounted (global parameter).
2. The y-intercept—controls the maximum discounting and the slope of the line, ranges from 1 (no discounting at all) to 0 (full discounting) (global parameter, default to 0).
3. Expected LOS—controls the point at which the score is no longer discounted (based either on base DRG alerts for the case or on a global parameter in the event of no base DRG alerts).

In some embodiments, the opportunity is multiplied by the LOS adjustment to arrive at the LOS adjusted opportunity. Unlike other adjustments, however, the LOS adjustment has nothing to do with calculating either the potential magnitude of the opportunity or the probability of realizing the opportunity. Rather, it is made to incentivize when reviews take place. As such, the parameter values can be configurable based on a desired policy of a customer or client of the system.

Incentivizing an Initial Review

In some cases, a customer or client of the system may want to incentivize a process where an initial review takes place (for example at the 24 to 48 hour mark) followed by a re-review prior to discharge. To accomplish this goal, the system may use two separate versions of this function with different values. The first version applies to cases which have never been reviewed and the second version applies to cases that have previously been reviewed.

For example, for cases that have never been reviewed, the system may use the values min LOS: 1 (do not review before 24 hours), y-intercept: 1 (no discounting at all beyond the first 24 hours), expected LOS: 2 (if discounting reach the maximum by the end of 48 hours) and for cases that have been reviewed, the system may use the values min LOS: 1 (do not review before 24 hours), y-intercept: 0 (full discounting), expected LOS: 5 (reaching the maximum by 5 days into the stay).

Example: Acme Hospital

| | |
|---|---|
| Minimum LOS before review: | 1 |
| y-intercept: | 0 |
| Mean expected LOS: | 5 |
| MS-DRG | GMLOS |
| pancreas, liver and shunt procedures w/ MCC | 11.337 |

Example: Patient Jane Smith

| | |
|---|---|
| Chief complaint: | cirrhosis w/ internal bleeding |
| LOS: | 6 |
| Attending: | Dr. Smith |
| Location: | ICU |
| Payer: | Allied Health |
| Procedures: | 06180J9 Bypass Portal Vein to Right Renal Vein with Synthetic Substitute, Open Approach |
| Medications: | Lactulose |
| Alerts: | Liver procedure (base DRG: pancreas, liver and shunt procedures, relative weight 1.828) Malnutrition (MCC, pancreas, liver and shunt procedures w/ MCC has relative weight 5.575) |
| Baseline: | 1.096 |
| Target: | 5.94 |
| Unadjusted Opportunity: | 4.844 |
| Probability Adjusted Opportunity: | 3.309 |
| Payer Adjusted Opportunity: | 2.978 |
| Location Adjusted Opportunity: | 3.871 |
| Location Adjusted Opportunity (last review): | .805 |
| Novelty Adjusted Opportunity: | 3.227 |
| Adjusted Opportunity: | 3.227 * ((1.0 − 0) * 6/11) + 0 = 1.760 |

Converting from an Adjusted Opportunity Size to a Score

Once the system calculated the estimated magnitude of the opportunity, the system can convert it to a score in the range 1 to 100 using a logistic function having a common "S" shape (sigmoid curve), also referred to as the standard logistic sigmoid function known to those skilled in the art. The advantages of using a sigmoid curve instead of direct linear scaling may include the following:

Outliers such as heart transplants with MCC (relative weight 26) are very large but also rare. Using a logistic function allows average sized opportunities to score towards the center of the scoring range (e.g., 50 in 0-100) instead of artificially low to accommodate the full potential range.

Using a logistic function eliminates the need to calculate a potential maximum opportunity size; as opportunity size approaches infinity, the score asymptotically approaches 100. If a future revision of the MS-DRG's increases the maximum relative weights possible or a new payer is introduced who pays better than any existing payer, rescaling the score is not required to accommodate such a change.

The function will be shifted such that the average opportunity size scores 50 and will be scaled such that most of the highest value opportunities score around 80. If historical distribution of adjustments is available, the system may select a value about one standard deviation away from the mean. Otherwise, a subject matter expert may be consulted to provide a realistic initial estimate.

Example: Patient Jane Smith, with a CDI Score Generated as a Function of an Adjusted Opportunity Size

| | |
|---|---|
| Chief complaint: | cirrhosis w/ internal bleeding |
| LOS: | 6 |
| Attending: | Dr. Smith |
| Location: | ICU |
| Payer: | Allied Health |
| Procedures: | 06180J9 Bypass Portal Vein to Right Renal Vein with Synthetic Substitute, Open Approach |
| Medications: | Lactulose |
| Alerts: | Liver procedure (base DRG: pancreas, liver and shunt procedures, relative weight 1.828) Malnutrition (MCC, pancreas, liver and shunt procedures w/ MCC has relative weight 5.575) |
| Baseline: | 1.096 |
| Target: | 5.94 |
| Unadjusted Opportunity: | 4.844 |
| Probability Adjusted Opportunity: | 3.309 |
| Payer Adjusted Opportunity: | 2.978 |
| Location Adjusted Opportunity: | 3.871 |
| Location Adjusted Opportunity (last review): | .805 |
| Novelty Adjusted Opportunity: | 3.227 |
| Adjusted Opportunity: | 1.760 |
| Score: | f(1.760) = 82 |

The CDI smart scoring process described above may be triggered by time or an event, according to some embodiments disclosed herein. For example, a CDI smart scoring process may be triggered when a patient's visit is updated (e.g., the patient's location is changed, the payer is changed, etc.); when an indicator is created; or when a time-based signal is received (e.g., once a night, etc.). Once triggered, the system may run the CDI smart scoring process for all visits that are still active. These trigger points are further illustrated in FIG. 3.

In the example illustrated, CDI data processing method 300 may include receiving, by a CDI smart scoring system such as system 205, real time medical data from a hospital data source (302) and settings such as configuration information for fragment definitions and alert rules described above (304). The system may process and analyze the real time medical data received from a hospital data source against the system's settings (306) and determine whether any threshold for a medical condition has been met (308). This may include, for instance, a particular patient's blood pressure reading or a blood test result. In some embodiments, a hospital or patient care facility may set a general threshold, while the patient's primary caregiver or attending physician may override such a setting on an individual basis. If no threshold is met, method 300 may loop back to process and analyze the next batch of data, as described above. If, however, a threshold is met, the system may proceed to determine whether an indicator is to be generated (310). If so, the system may generate an indicator (312). Otherwise, method 300 ends and no CDI score is updated (314).

Figure 3:
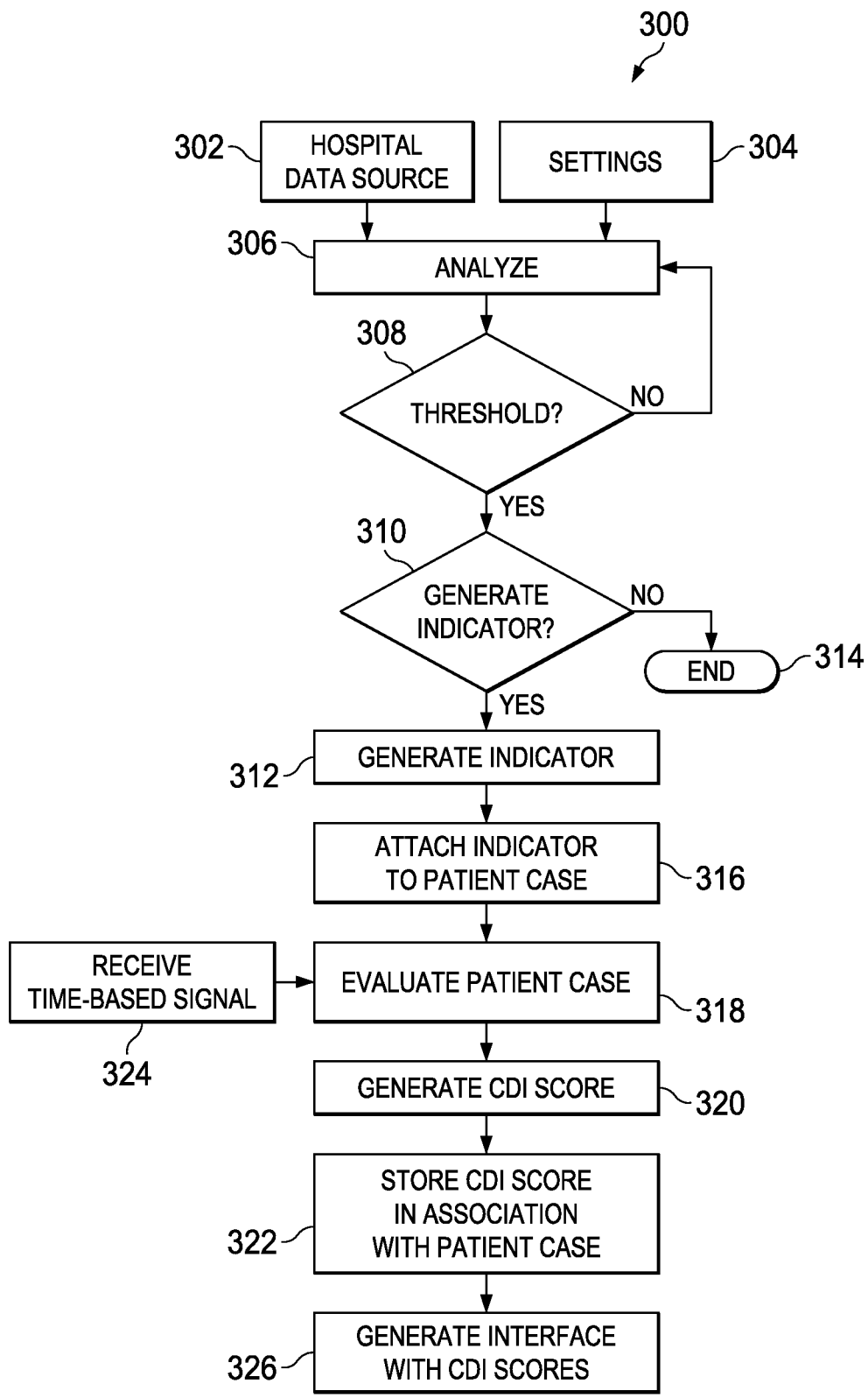
FIG. 3 is a flowchart illustrating one example of a CDI data processing method including a CDI smart scoring according to some embodiments disclosed herein.

The generated indicator is attached (e.g., by alert engine 224 described above) to a patient's case (316). This can be done by creating a row or otherwise inserting an entry in an indicator table associated with the patient's case (e.g., via a visit ID). CDI scoring engine 240 may receive a notification directly from alert engine 224 that a new indicator has been generated, or it may monitor (e.g., via a listener) events broadcasted by alert engine 224 and learn that a new indicator has been generated. In response, CDI scoring engine 240 may pull the patient's case (e.g., using the visit ID associated with the newly generated indicator) and evaluate the patient's case for an opportunity to improve clinical documentation associated with the patient's case (318). This CDI evaluation may implement the CDI smart scoring algorithm described above. As illustrated in FIG. 3, in some embodiments, the CDI evaluation may be performed periodically, regardless of whether an indicator has been generated or whether a change in a patient's status or location is received (324).

Based on the CDI evaluation, the system may generate a CDI score as described above (320) and store the generated CDI score in association with the patient case (322). In some embodiments, the system may generate a graphical user interface for presenting the CDI scores to CDI specialists (326).

Figure 4:
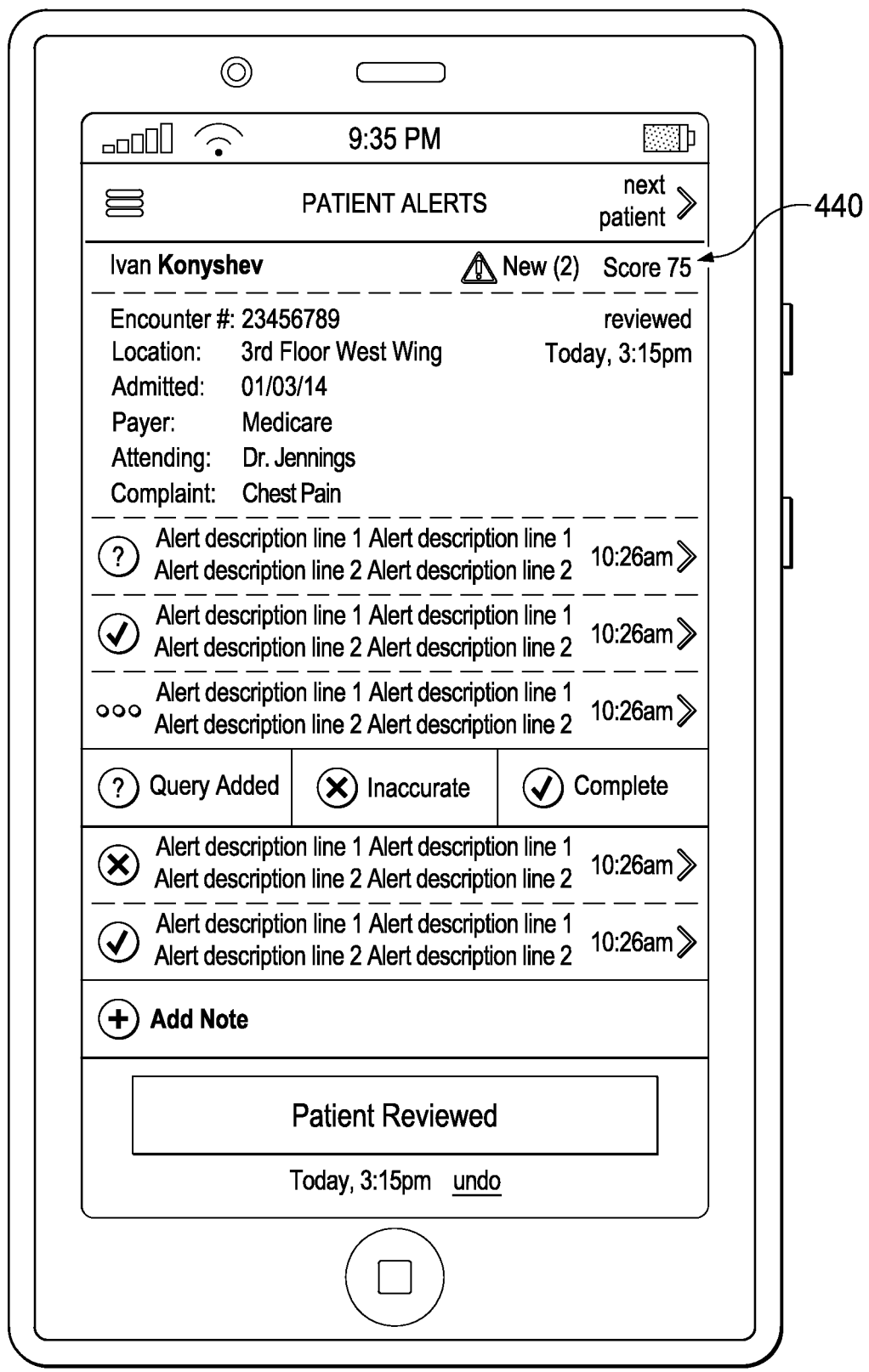
FIG. 4 depicts a diagrammatic representation of one example of a graphical user interface showing a CDI score generated by a CDI smart scoring system according to some embodiments disclosed herein.

FIG. 4 depicts a diagrammatic representation of one example of graphical user interface 400 showing CDI score 440 generated by a CDI smart scoring system according to some embodiments disclosed herein. Graphical user interface 400 may be configured for running on various computing devices. Furthermore, graphical user interface 400 may be configured for a CDI specialist to perform a CDI review. In some cases, explanation icons may be used to provide context on why a patient may be scored unusually high or low, thereby giving the user additional confidence in the CDI scoring algorithm. In the example illustrated, a patient name is provided along with a variety of designated alerts. Graphical user interface 400 may be further configured for a CDI specialist to send a query to a medical practitioner, such as an attending physician regarding a particular alert (or an indicator, which is a particular type of alert) generated by the CDI smart scoring system In some embodiments, patients may be ranked according to their CDI scores to allow CDI specialists a quick way to prioritize cases for CDI review. For example, FIG. 5 depicts a diagrammatic representation of another example of a graphical user interface showing a ranking or prioritization, by score, of multiple patients. In some embodiments, the ranking also identifies a cause of alerts and the time that the new scoring was performed. In addition, in some embodiments, the GUI allows a CDI specialist to mark when the case was last reviewed. In some embodiments, the CDI specialist may input a query, e.g., to an attending physician. Typically, once reviewed, the patient may be removed from a list for a predetermined interval (e.g., 24 hours), referred to as a "quiet time," unless a new event has occurred.

Figure 6:
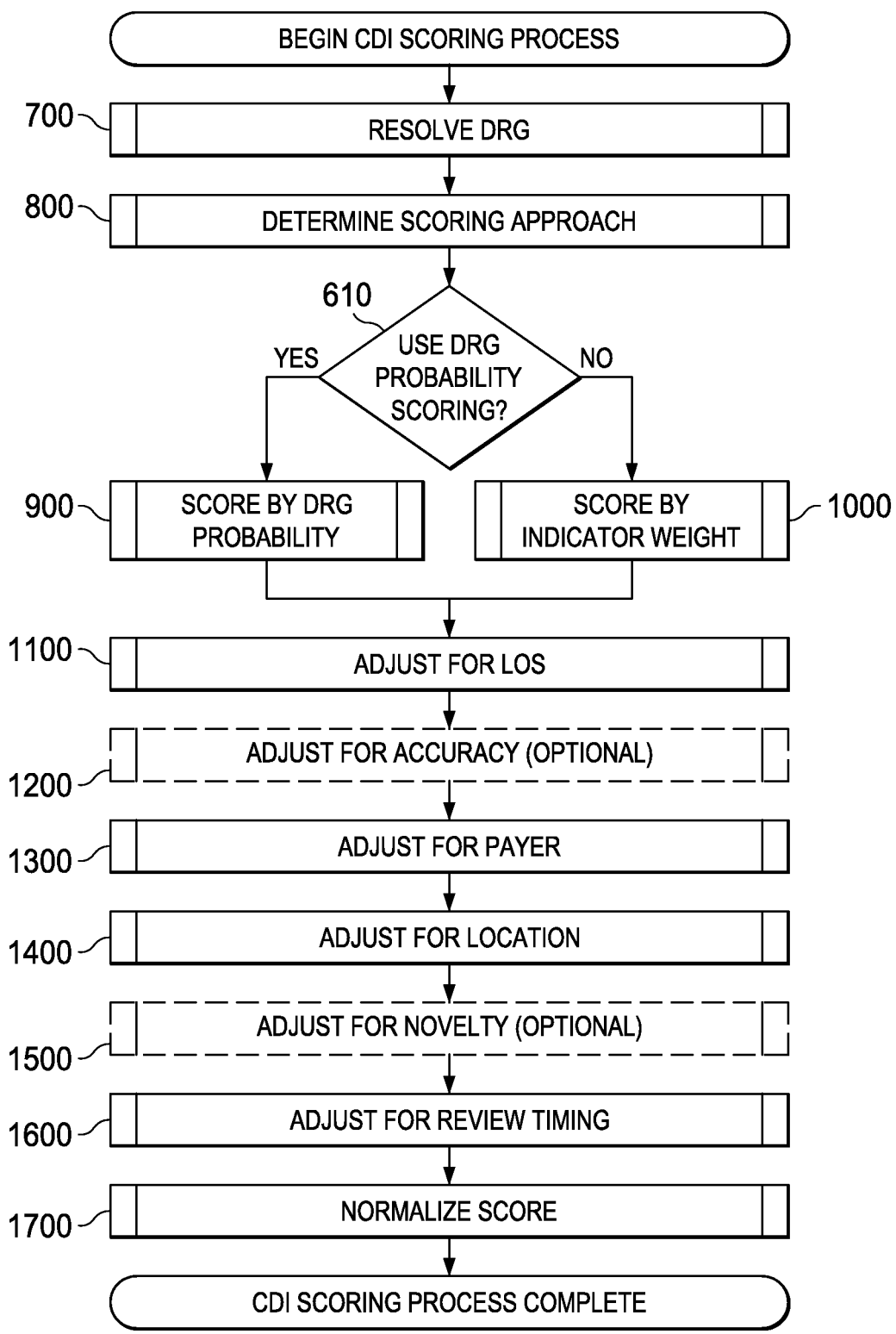
FIG. 6 is a flowchart illustrating one example of a CDI smart scoring method according to some embodiments disclosed herein.

As illustrated in FIG. 6, the above-described CDI smart scoring process may be implemented in many ways. In some embodiments, CDI smart scoring method 600 may be initiated responsive to any of the triggers (or triggering events) discussed above (e.g., a change in a patient's location or attending physician, an indicator associated with the patient's health or medical condition, a timed call from a system component such as a job scheduler, etc.).

Figure 7A:
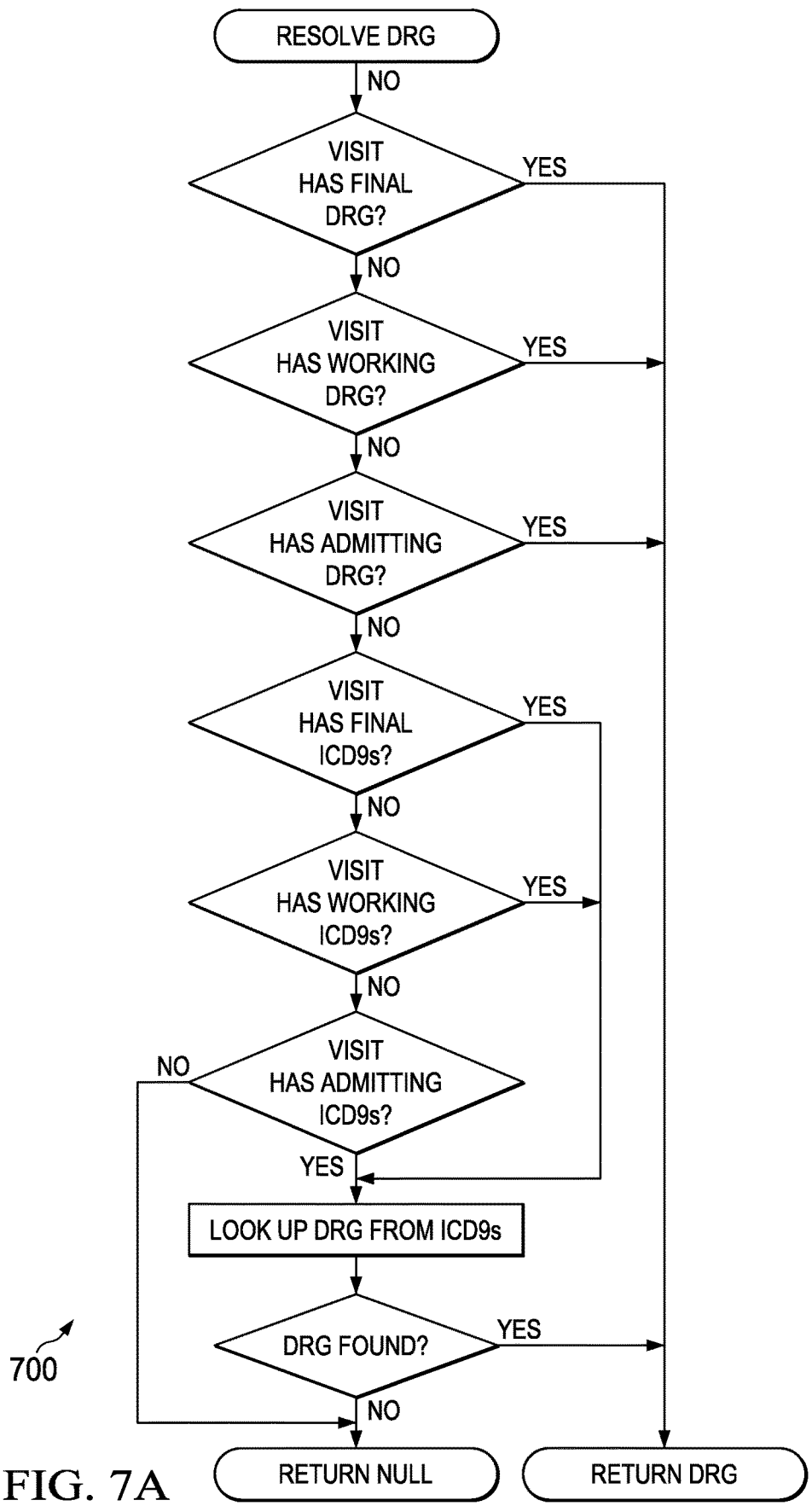
FIG. 7A is a flowchart illustrating one example of a process for resolving Diagnosis-Related Group (DRG) code according to some embodiments disclosed herein.
Figure 7B:
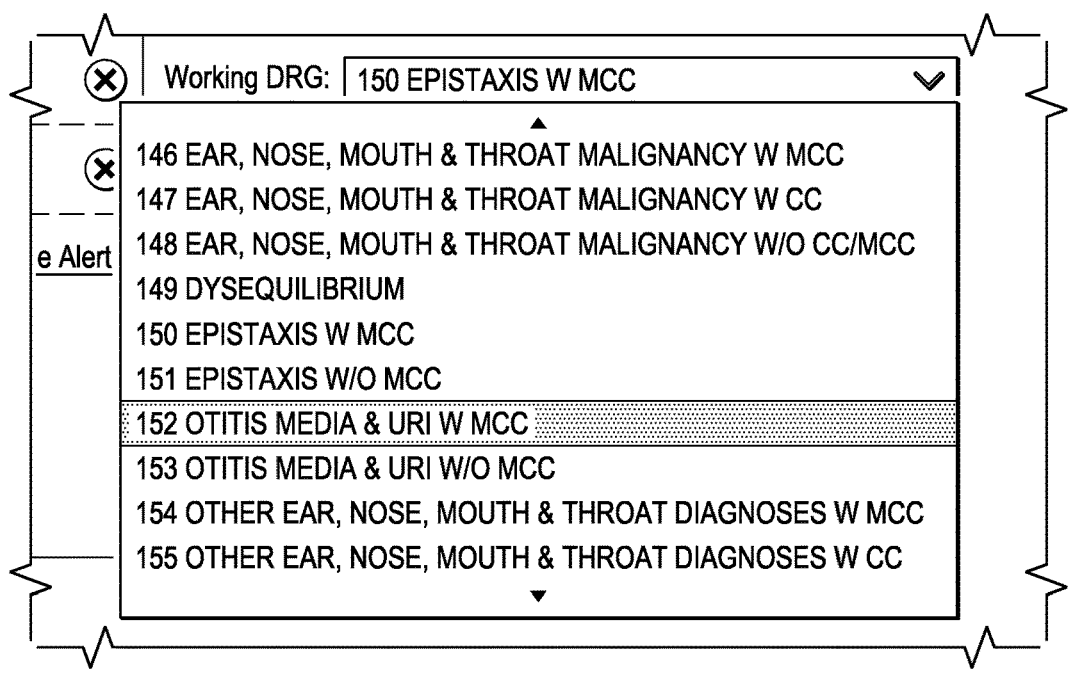
FIG. 7B depicts a diagrammatic representation of one example of a graphical user interface showing user-selectable working DRG codes according to some embodiments disclosed herein.

Method 600 may include resolving whether an DRG code has been assigned or otherwise applies to a patient's current stay (referred to as a "visit") at a hospital or healthcare facility. An example of process 700 for resolving a DRG code for the patient is illustrated in FIG. 7A. Process 700 may include determining whether a visit ID associated with the patient has a final DRG code, a working DRG code, or an admitting DRG code. If no DRG code could be found, process 700 may proceed to search for a possible International Classification of Diseases (ICD), Ninth Revision, code (e.g., whether a final ICD9 code, a working ICD9 code, or an admitting ICD9 code could be found). If an ICD9 code is found, it could be used to look up a DRG. When no DRG or ICD9 code could be found, process 700 ends and a user of the system may be asked to select or assign a working DRG code. As discussed above, ICD9 can be replaced by future revisions such as ICD10, etc. without affecting process 700. FIG. 7B depicts a diagrammatic representation of one example of graphical user interface 710 showing user-selectable working DRG codes according to some embodiments disclosed herein.

Figure 8:
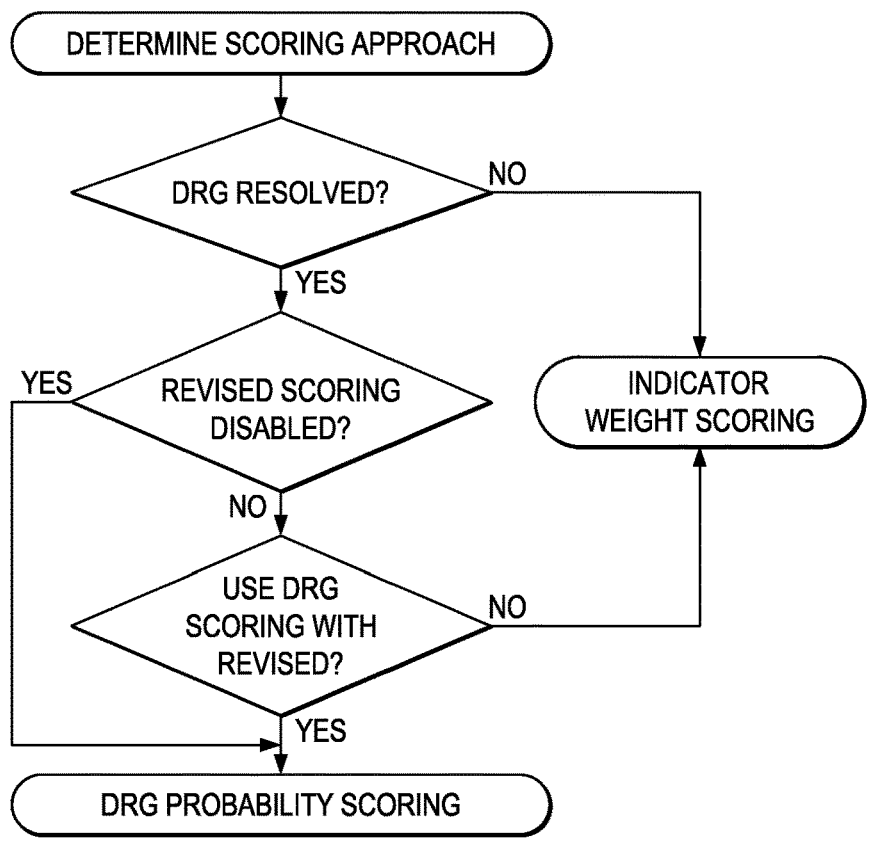
FIG. 8 is a flowchart illustrating one example of a process for determining a CDI scoring approach according to some embodiments disclosed herein.

In some embodiments, method 600 may optionally include determining an appropriate scoring approach for calculating a CDI score. An example of process 800 for determining a CDI scoring approach is illustrated in FIG. 8. As illustrated, if a DRG code could not be resolved, a CDI score may be computed using an indicator weight. Alternatively, if a DRG code could be resolved, but could not be used with a revised CDI score, a CDI score may be computed using an indicator weight. Otherwise, the resolved DRG code is used. Process 800 can be employed in some cases as a mechanism to force the system to use the indicator weight path and then to override that decision.

Figure 9:
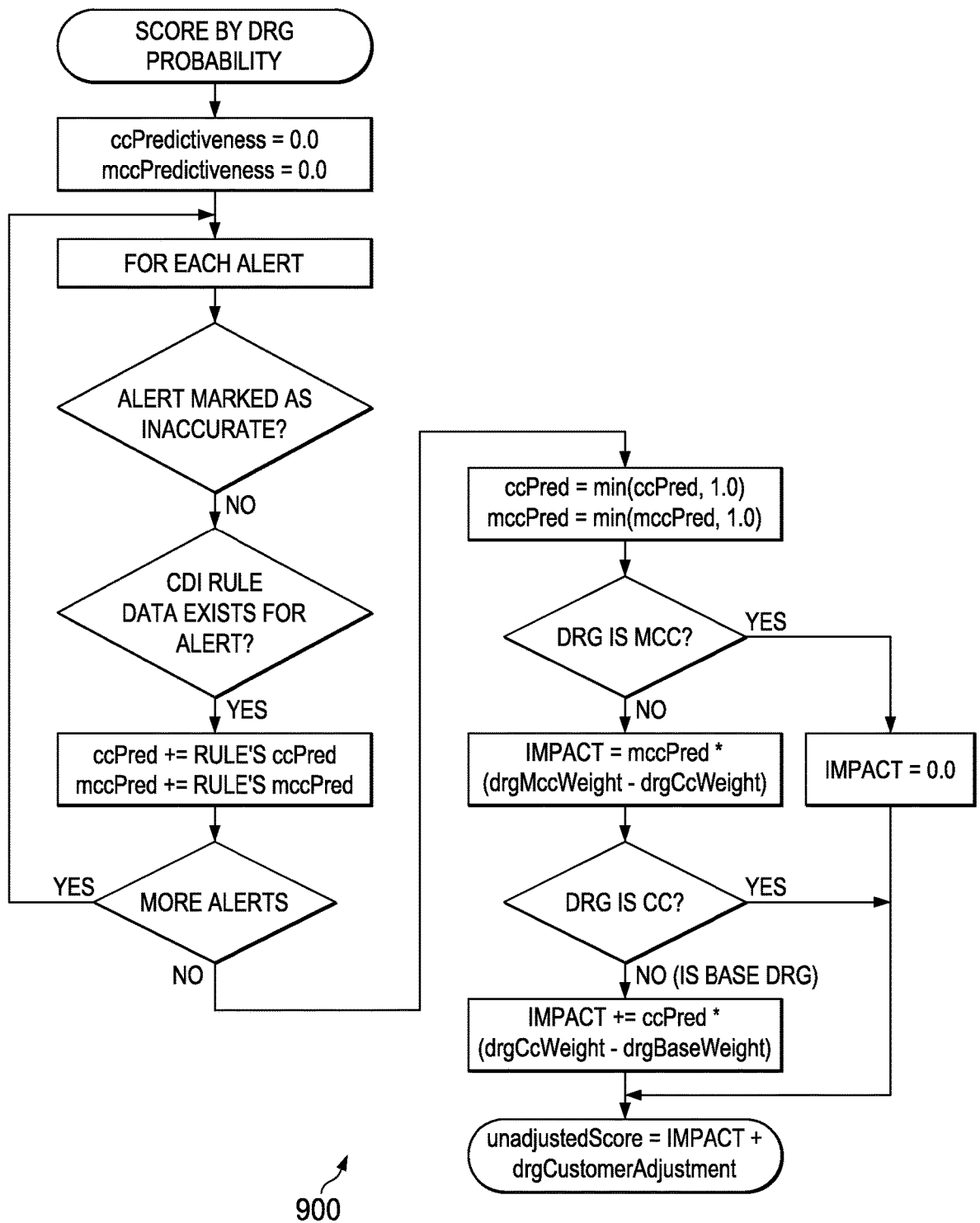
FIG. 9 is a flowchart illustrating one example of a process for scoring by DRG probability according to some embodiments disclosed herein.
Figure 10:
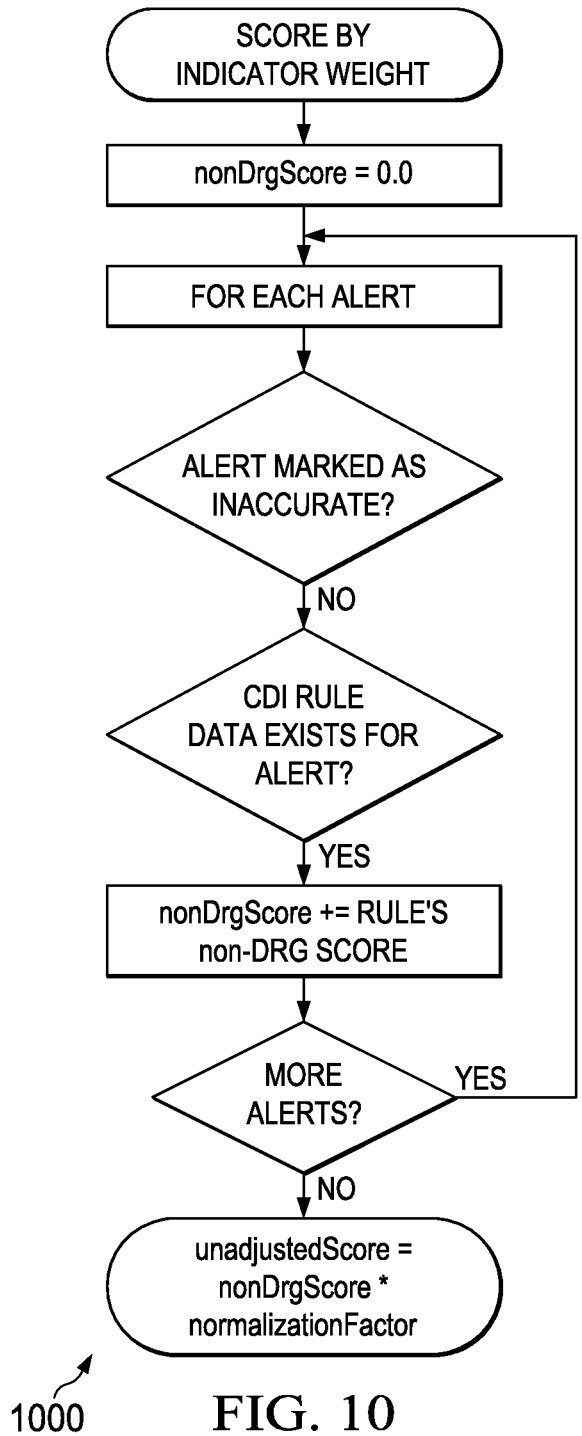
FIG. 10 is a flowchart illustrating one example of a process for scoring by indicator weight according to some embodiments disclosed herein.

FIG. 9 is a flowchart illustrating one example of process 900 for scoring by DRG probability according to some embodiments disclosed herein. FIG. 10 is a flowchart illustrating one example of process 1000 for scoring by indicator weight according to some embodiments disclosed herein. Both process 900 and process 1000 analyze each alert (e.g., an indicator generated by alert engine 224) and factor in medical conditions associated with the patient, including secondary conditions and severity levels as described above, to produce a CDI score that measures the chance (referred to as an opportunity in the example CDI model described above) to improve the clinical documentation of the patient case under analysis.

Figure 11A:
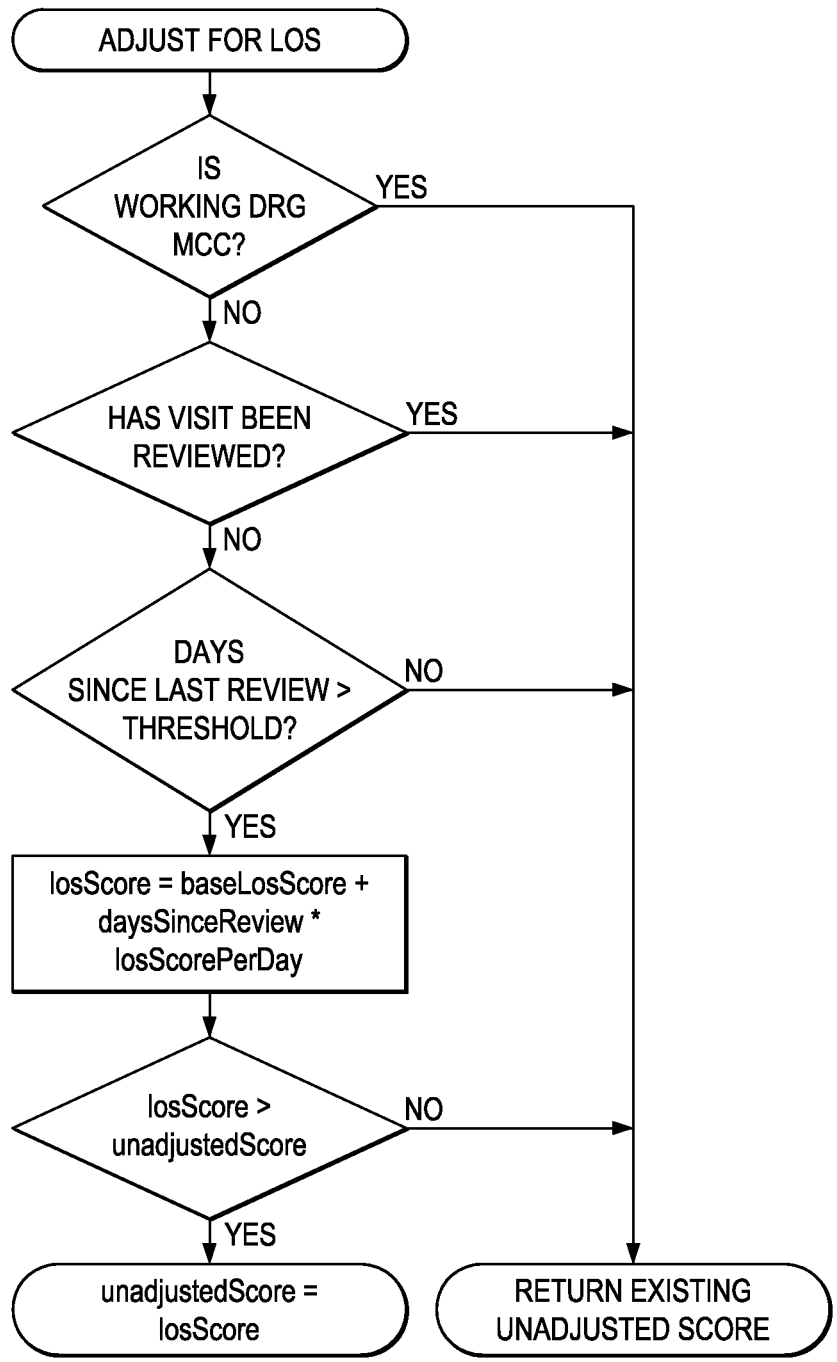
FIG. 11A is a flowchart illustrating one example of a process for determining a length of stay (LOS) adjustment to a system-generated CDI score according to some embodiments disclosed herein.
Figure 11B:
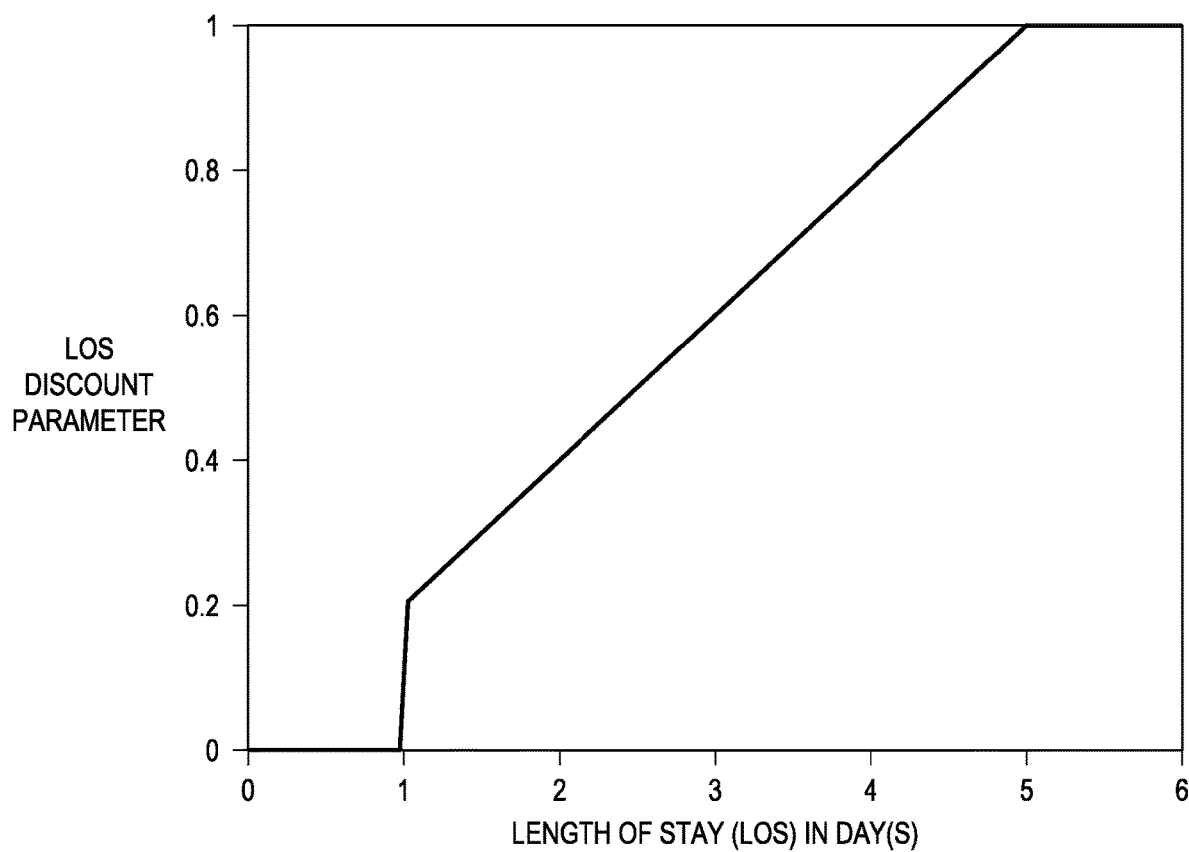
FIG. 11B is a plot diagram illustrating one example of a LOS discount function according to some embodiments disclosed herein.
Figure 12:
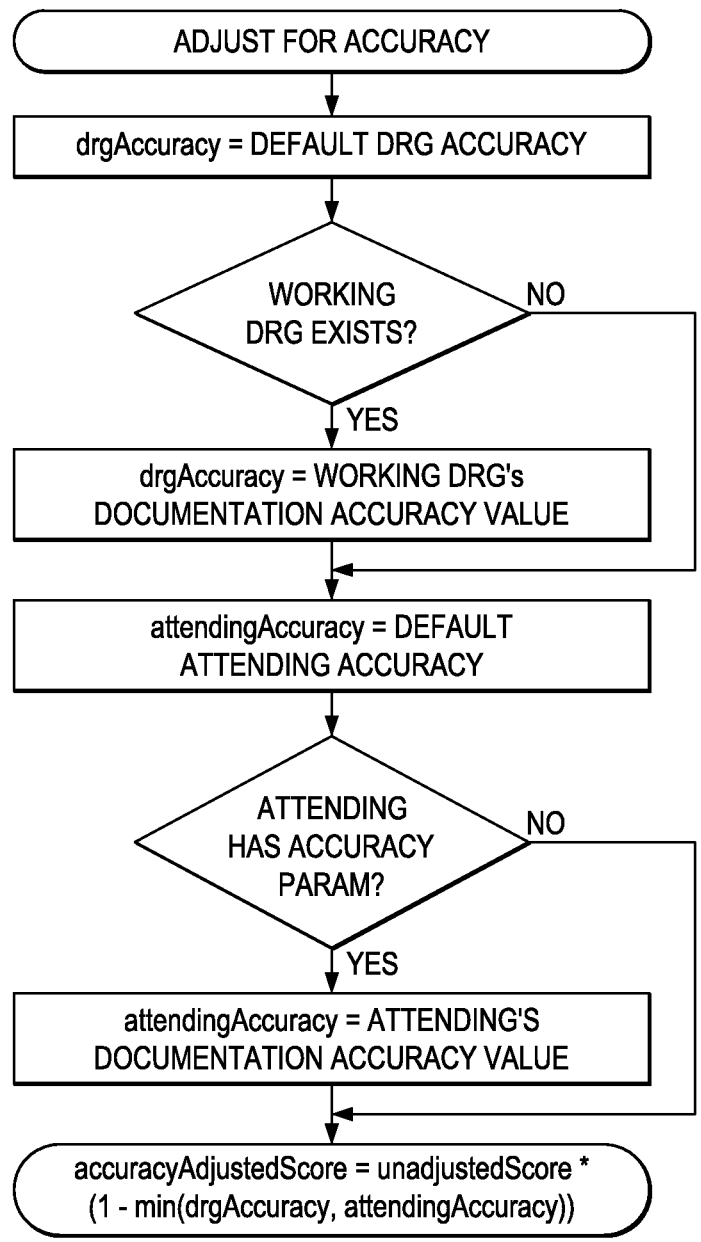
FIG. 12 is a flowchart illustrating one example of an optional process for determining a documentation accuracy adjustment to a system-generated CDI score according to some embodiments disclosed herein.
Figure 13:
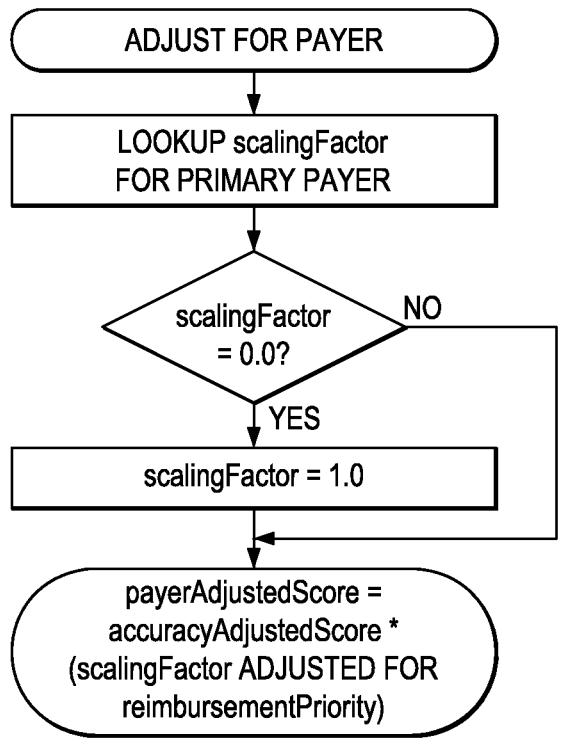
FIG. 13 is a flowchart illustrating one example of a process for determining a payer adjustment to a system-generated CDI score according to some embodiments disclosed herein.
Figure 14:
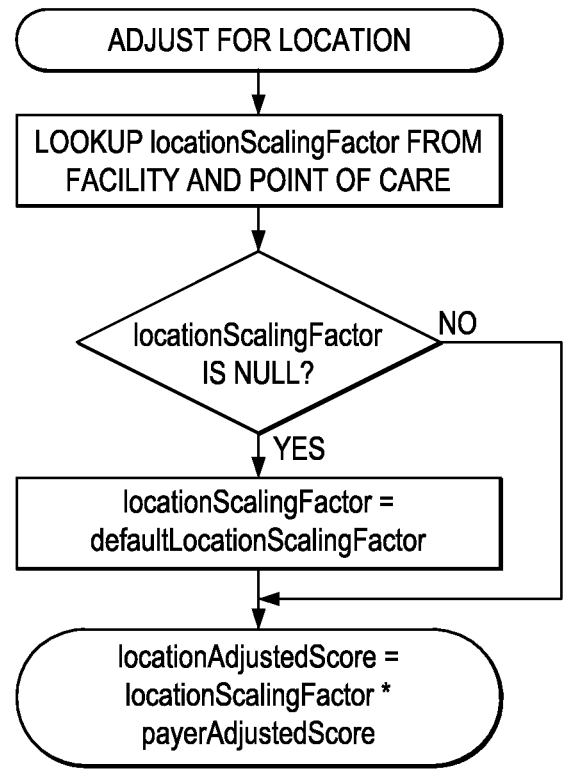
FIG. 14 is a flowchart illustrating one example of a process for determining a location adjustment to a system-generated CDI score according to some embodiments disclosed herein.
Figure 15:
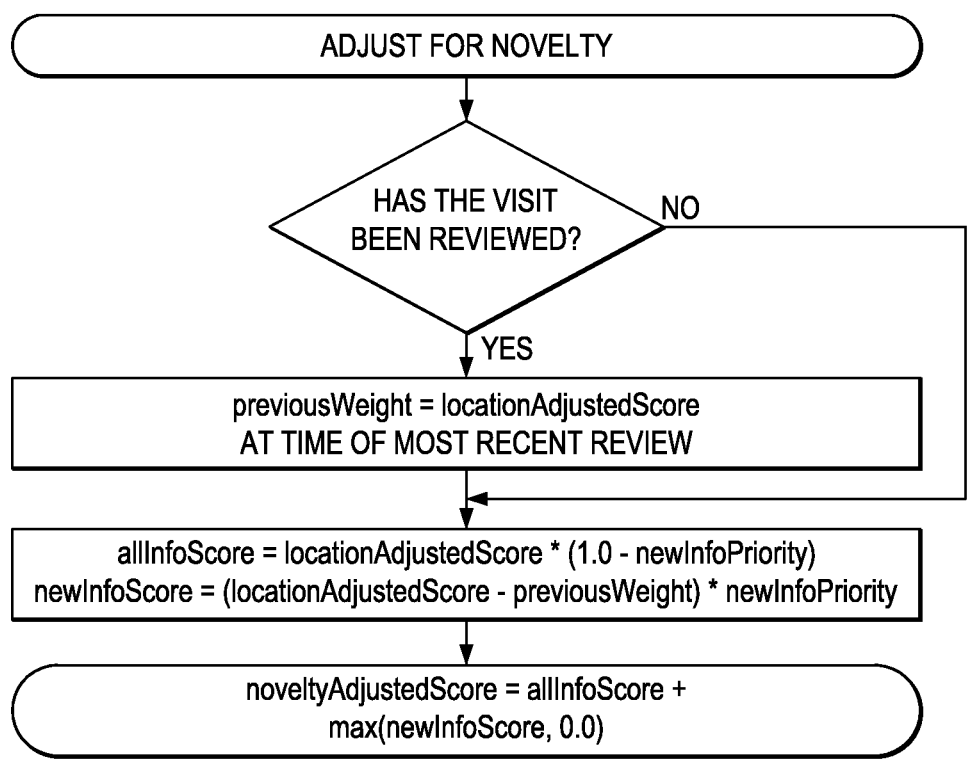
FIG. 15 is a flowchart illustrating one example of an optional process for determining a new visit adjustment to a system-generated CDI score according to some embodiments disclosed herein.
Figure 16:
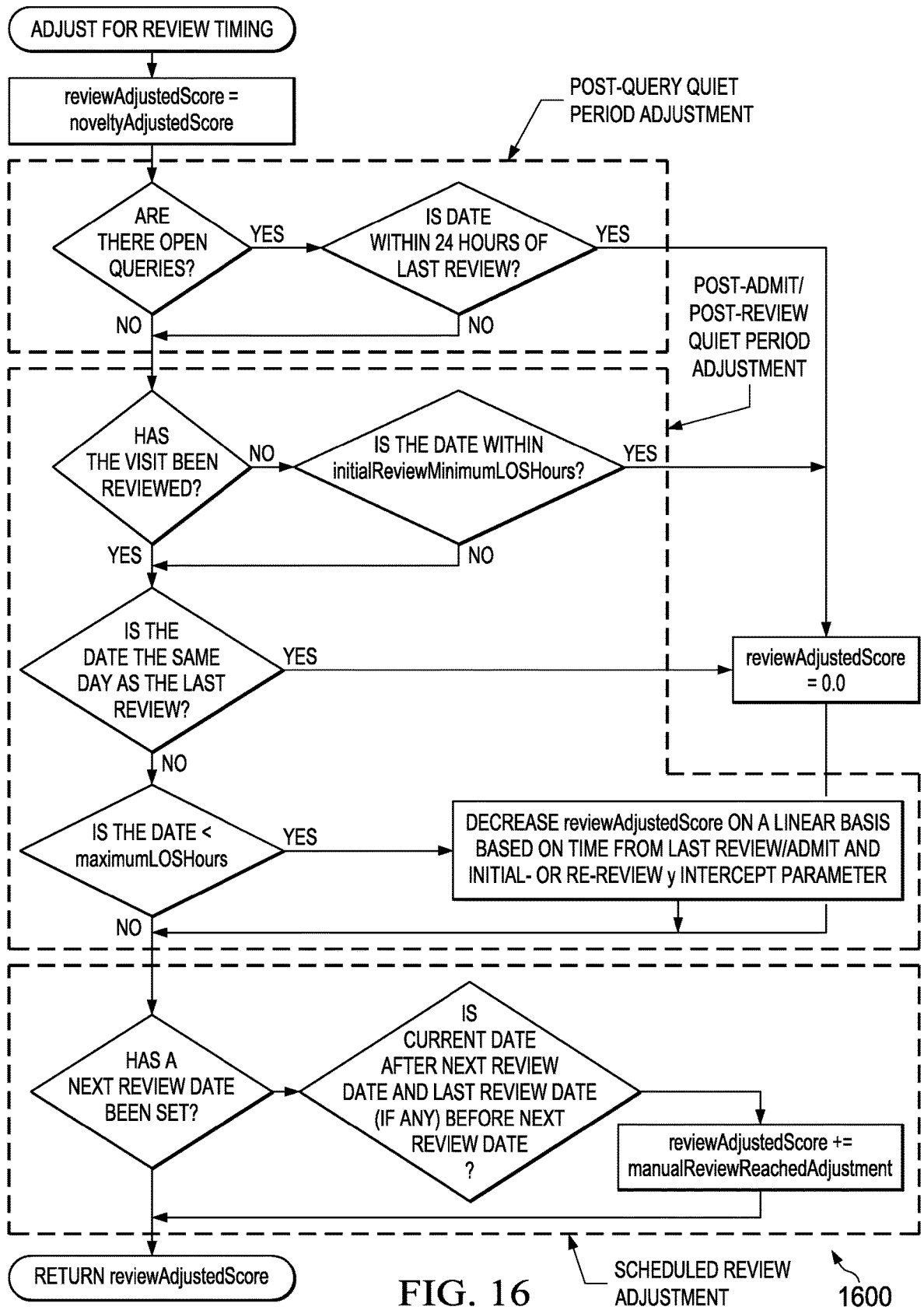
FIG. 16 is a flowchart illustrating one example of a process for determining a review timing adjustment to a system-generated CDI score according to some embodiments disclosed herein.
Figure 17:
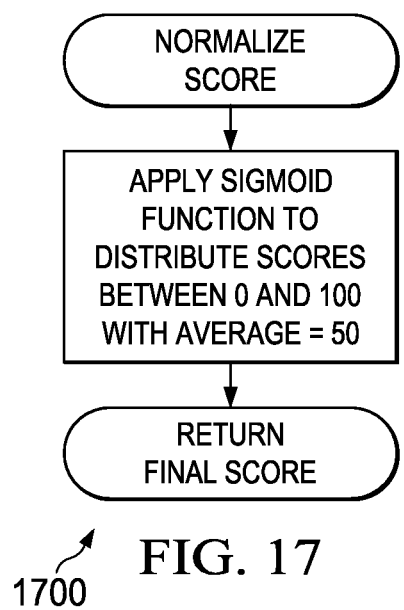
FIG. 17 is a flowchart illustrating one example of a process for normalizing a system-generated CDI score according to some embodiments disclosed herein.

As discussed above and illustrated in FIG. 6, the CDI score thus generated (by process 900 or process 1000) can be adjusted in many ways, for instance, by a length of stay (LOS) adjustment (1100), an accuracy adjustment (1200), a payer adjustment (1300), a location adjustment (1400), a novelty adjustment (1500), and/or a review timing adjustment (1600). One or more of these adjustments may be optional or replaced with information collected or generated from another part of the underlying system. For example, as illustrated in FIG. 11A, no LOS adjustment may be applicable to the CDI score if the current LOS does not exceed a predefined threshold. FIG. 11B is a plot diagram illustrating one example of a LOS discount function that may be used in determining an LOS adjustment. In this example, the LOS discount function assumes a threshold of 1 for the minimum LOS, 0 for y-intercept, and 5 for an expected LOS. As another example, if a payer does not care about documentation accuracy, process 1200 for determining a documentation accuracy adjustment may be made optional.

Likewise, in some embodiments, only new indicators may be considered and thus process 1500 for determining a new visit adjustment may be eliminated. Details for these processes 1100, 1200, 1300, 1400, 1500, and 1600 are described above with regard to the CDI smart scoring algorithm. The adjusted CDI score is then normalized into a predefined range (e.g., 0-100). At this time, process 600 is complete and the final (adjusted and normalized) CDI score is stored in the patient's case. As an example, the CDI score may be attached in a column on a Visit table associated with the patient's case. This is the current CDI score for the patient which may then be presented to a CDI specialist via a user interface running on a computing device communicatively connected to the CDI smart scoring system disclosed herein.

Multiple CDI scores for different patient cases may be displayed in a prioritized fashion (e.g., shows what a score is or shows that there is no score for a patient). The CDI specialist may interact with the system via the user interface (e.g., selecting a case for review, indicating that a case has been reviewed, sending a query about the patient to the attending physician about an alert, etc.). Notice that when a case has been reviewed by a CDI specialist, the case may be re-evaluated and the CDI score may be reset at that point.

As described above, the patient case may be evaluated and the CDI score may be updated (revised) anytime new information about the patient is received. This information can include what indicators have been found for the patient, what the patient's location is, potentially what the attending physician for the patient is, etc. Additionally, the patient case may be evaluated and the CDI score may be updated on a periodic basis. This case evaluation/CDI scoring schedule can be configurable by an authorized user such as a system administrator. Different CDI models may be implemented, depending upon hospital policy. One example CDI model is referred to as the "follow the patient" model. Some hospitals assign particular people to a particular location within the hospital (e.g., "Mary is responsible for Floor Two" so Mary (a nurse or a CDI specialist) reviews cases for patients that are on Floor Two) or based on a particular hospital service (e.g., "Jane is responsible for cardiology patients" so Jane reviews cases for cardiology patients). Another example CDI model is referred to as the "common pool of people responsible for a set of cases" model: A manager assigns John to review 15 cases, Joe to review 15 cases, and Sue to review 15 cases today, so together they are a CDI team responsible for 45 cases. Alternatively, they may be responsible for reviewing a set number of cases per month.

To this end, different implementation scenarios may occur:
  Once a CDI specialist reviewed a patient's case, that CDI specialist "owns" that patient (i.e., the system associates the reviewer's identifier to the patient identifier) and future/follow up reviews of any case associated with that patient will be performed by the CDI owner. How that CDI owner gets notified may be determined based on hospital policy. For example, a location based policy may specify that this location is assigned to Sue so Sue is assigned by the system as the CDI owner when a case comes in that Sue covers the location of the case.
  The system does not associate a reviewer with any particular patient and assigns based on some factors (e.g., the location of the patient, the hospital service provided to the patient, etc.). The hospital service information is provided by the hospital in the incoming message to the system. This allows the system to filter by location what cases are to be displayed for CDI review.

The system automatically assigns cases for CDI review based on CDI scores associated with those cases. For example, a team of five CDI specialists may get an equal distribution of patient cases to review based on CDI scores associated with those cases. Alternatively, the system may assign cases following a hospital's policy. For example, a hospital may have a visit assignment policy that specifies, for an arbitrary set of criteria (e.g., a hospital location or service), if the set of criteria applies to a visit, then the case (per the visit ID) is to be assigned to a particular CDI specialist and in what role (in this case, as a "CDI owner"). The system may evaluate these criteria and assign the cases for CDI review accordingly.

This default setting of a CDI owner may be overridden by user action. For example, when a CDI specialist selects and reviews a case, the CDI specialist may thereafter "own" the case (i.e., permanently attached to the case), depending upon the system setting that reflects the particular hospital policy (e.g., follow the patient or the location or the hospital service, etc.).

This process flow may end at the backend when the score is generated and attached to the Visit table. The process then flows to the frontend (e.g., distribute to and display on computing devices over a network) and depending upon user action, the Visit table may be updated, for instance, to reflect the new CDI owner.

Embodiments disclosed herein can be implemented in many ways. For example, in some embodiments, indicator weights may be assigned (e.g., by consulting with subject matter experts). In some embodiments, indicator weights may be computed based on statistics calculated across data points representing how predictive each of the indicators is.

Furthermore, in some embodiments, the CDI smart scoring method described above (which examines clinical evidence received by the system to determine how to prioritize cases for CDI review) may be adapted to factor in the amount of effort needed by a CDI specialist to review a patient case due to the size/amount of documentation involved. A case size adjustment may be determined based at least in part on statistics collected about how much documentation there is for a patient case. For example, a case that has been in a hospital for 50 days and has 300 pages of documentation requires a much bigger effort for a CDI specialist to review that than a case that just arrived yesterday.

Referring to FIG. 2B, in some embodiments, documentation processor 250 may be configured for obtaining documentation from HL7 database 206, determining the amount of documentation for a case, and inserting records on the amount (referred to as observation orders) into database 225 for the associated visit. In this way, the CDI smart scoring process described above may also examine the total amount of documents associated with that visit in producing a CDI score for the case.

In some embodiments, the system may additionally consider sufficiency in documentation already exists in a case and determine whether sufficient documentation indicates that this case has been documented. That is, the system can identify cases that do not need to be reviewed, eliminating time that may be wasted in performing unnecessary CDI reviews and further increasing the overall efficiency of the CDI review process.

Referring to FIG. 2C, in some embodiments, documentation processor 250 may be configured for obtaining documentation from HL7 database 206, analyzing the documents to extract "concepts" (e.g., procedures or procedure code extracted via a natural language processing tool), determining which of those concepts are relevant to specific patient conditions, updating the conditions appropriately, and adjusting the CDI score based both upon the strength of the evidence that a condition exists and the potential that the condition is already documented and therefore does not need to be reviewed. As a result, each visit table is timely updated so to have complete and comprehensive documentation that the system knows or learns about a particular patient.

Although the invention has been described with respect to specific embodiments thereof, these embodiments are merely illustrative, and not restrictive of the invention. The description herein of illustrated embodiments of the invention, including the description in the Abstract and Summary, is not intended to be exhaustive or to limit the invention to the precise forms disclosed herein (and in particular, the inclusion of any particular embodiment, feature or function within the Abstract or Summary is not intended to limit the scope of the invention to such embodiment, feature or function). Rather, the description is intended to describe illustrative embodiments, features and functions in order to provide a person of ordinary skill in the art context to understand the invention without limiting the invention to any particularly described embodiment, feature or function, including any such embodiment feature or function described in the Abstract or Summary. While specific embodiments of, and examples for, the invention are described herein for illustrative purposes only, various equivalent modifications are possible within the spirit and scope of the invention, as those skilled in the relevant art will recognize and appreciate. As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the invention.

Reference throughout this specification to "one embodiment", "an embodiment", or "a specific embodiment" or similar terminology means that a particular feature, structure, or characteristic described in connection with the embodiment is included in at least one embodiment and may not necessarily be present in all embodiments. Thus, respective appearances of the phrases "in one embodiment", "in an embodiment", or "in a specific embodiment" or similar terminology in various places throughout this specification are not necessarily referring to the same embodiment. Furthermore, the particular features, structures, or characteristics of any particular embodiment may be combined in any suitable manner with one or more other embodiments. It is to be understood that other variations and modifications of the embodiments described and illustrated herein are possible in light of the teachings herein and are to be considered as part of the spirit and scope of the invention.

In the description herein, numerous specific details are provided, such as examples of components and/or methods, to provide a thorough understanding of embodiments of the invention. One skilled in the relevant art will recognize, however, that an embodiment may be able to be practiced without one or more of the specific details, or with other apparatus, systems, assemblies, methods, components, materials, parts, and/or the like. In other instances, well-known structures, components, systems, materials, or operations are not specifically shown or described in detail to avoid obscuring aspects of embodiments of the invention. While the invention may be illustrated by using a particular embodiment, this is not and does not limit the invention to any particular embodiment and a person of ordinary skill in the art will recognize that additional embodiments are readily understandable and are a part of this invention.

Embodiments discussed herein can be implemented in a computer communicatively coupled to a network (for example, the Internet), another computer, or in a standalone computer. As is known to those skilled in the art, a suitable computer can include a central processing unit ("CPU"), at least one read-only memory ("ROM"), at least one random access memory ("RAM"), at least one hard drive ("HD"), and one or more input/output ("I/O") device(s). The I/O devices can include a keyboard, monitor, printer, electronic pointing device (for example, mouse, trackball, stylus, touch pad, etc.), or the like.

ROM, RAM, and HD are computer memories for storing computer-executable instructions executable by the CPU or capable of being compiled or interpreted to be executable by the CPU. Suitable computer-executable instructions may reside on a computer readable medium (e.g., ROM, RAM, and/or HD), hardware circuitry or the like, or any combination thereof. Within this disclosure, the term "computer readable medium" is not limited to ROM, RAM, and HD and can include any type of data storage medium that can be read by a processor. For example, a computer-readable medium may refer to a data cartridge, a data backup magnetic tape, a floppy diskette, a flash memory drive, an optical data storage drive, a CD-ROM, ROM, RAM, HD, or the like. The processes described herein may be implemented in suitable computer-executable instructions that may reside on a computer readable medium (for example, a disk, CD-ROM, a memory, etc.). Alternatively, the computer-executable instructions may be stored as software code components on a direct access storage device array, magnetic tape, floppy diskette, optical storage device, or other appropriate computer-readable medium or storage device.

Any suitable programming language can be used to implement the routines, methods or programs of embodiments of the invention described herein, including C, C++, Java, JavaScript, HTML, or any other programming or scripting code, etc. Other software/hardware/network architectures may be used. For example, the functions of the disclosed embodiments may be implemented on one computer or shared/distributed among two or more computers in or across a network. Communications between computers implementing embodiments can be accomplished using any electronic, optical, radio frequency signals, or other suitable methods and tools of communication in compliance with known network protocols.

Different programming techniques can be employed such as procedural or object oriented. Any particular routine can execute on a single computer processing device or multiple computer processing devices, a single computer processor or multiple computer processors. Data may be stored in a single storage medium or distributed through multiple storage mediums, and may reside in a single database or multiple databases (or other data storage techniques). Although the steps, operations, or computations may be presented in a specific order, this order may be changed in different embodiments. In some embodiments, to the extent multiple steps are shown as sequential in this specification, some combination of such steps in alternative embodiments may be performed at the same time. The sequence of operations described herein can be interrupted, suspended, or otherwise controlled by another process, such as an operating system, kernel, etc. The routines can operate in an operating system environment or as stand-alone routines. Functions, routines, methods, steps and operations described herein can be performed in hardware, software, firmware or any combination thereof.

Embodiments described herein can be implemented in the form of control logic in software or hardware or a combination of both. The control logic may be stored in an information storage medium, such as a computer-readable medium, as a plurality of instructions adapted to direct an information processing device to perform a set of steps disclosed in the various embodiments. Based on the disclosure and teachings provided herein, a person of ordinary skill in the art will appreciate other ways and/or methods to implement the invention.

It is also within the spirit and scope of the invention to implement in software programming or code an of the steps, operations, methods, routines or portions thereof described herein, where such software programming or code can be stored in a computer-readable medium and can be operated on by a processor to permit a computer to perform any of the steps, operations, methods, routines or portions thereof described herein. The invention may be implemented by using software programming or code in one or more digital computers, by using application specific integrated circuits, programmable logic devices, field programmable gate arrays, optical, chemical, biological, quantum or nanoengineered systems, components and mechanisms may be used. In general, the functions of the invention can be achieved by any means as is known in the art. For example, distributed, or networked systems, components and circuits can be used. In another example, communication or transfer (or otherwise moving from one place to another) of data may be wired, wireless, or by any other means.

A "computer-readable medium" may be any medium that can contain, store, communicate, propagate, or transport the program for use by or in connection with the instruction execution system, apparatus, system or device. The computer readable medium can be, by way of example only but not by limitation, an electronic, magnetic, optical, electromagnetic, infrared, or semiconductor system, apparatus, system, device, propagation medium, or computer memory. Such computer-readable medium shall be machine readable and include software programming or code that can be human readable (e.g., source code) or machine readable (e.g., object code). Examples of non-transitory computer-readable media can include random access memories, read-only memories, hard drives, data cartridges, magnetic tapes, floppy diskettes, flash memory drives, optical data storage devices, compact-disc read-only memories, and other appropriate computer memories and data storage devices. In an illustrative embodiment, some or all of the software components may reside on a single server computer or on any combination of separate server computers. As one skilled in the art can appreciate, a computer program product implementing an embodiment disclosed herein may comprise one or more non-transitory computer readable media storing computer instructions translatable by one or more processors in a computing environment.

A "processor" includes any, hardware system, mechanism or component that processes data, signals or other information. A processor can include a system with a central processing unit, multiple processing units, dedicated circuitry for achieving functionality, or other systems. Processing need not be limited to a geographic location, or have temporal limitations. For example, a processor can perform its functions in "real-time," "offline," in a "batch mode," etc. Portions of processing can be performed at different times and at different locations, by different (or the same) processing systems.

It will also be appreciated that one or more of the elements depicted in the drawings/figures can also be implemented in a more separated or integrated manner, or even removed or rendered as inoperable in certain cases, as is useful in accordance with a particular application. Additionally, any signal arrows in the drawings/figures should be considered only as exemplary, and not limiting, unless otherwise specifically noted.

As used herein, the terms "comprises," "comprising," "includes," "including," "has," "having," or any other variation thereof, are intended to cover a non-exclusive inclusion. For example, a process, product, article, or apparatus that comprises a list of elements is not necessarily limited only those elements but may include other elements not expressly listed or inherent to such process, product, article, or apparatus.

Furthermore, the term "or" as used herein is generally intended to mean "and/or" unless otherwise indicated. For example, a condition A or B is satisfied by any one of the following: A is true (or present) and B is false (or not present), A is false (or not present) and B is true (or present), and both A and B are true (or present). As used herein, including the claims that follow, a term preceded by "a" or "an" (and "the" when antecedent basis is "a" or "an") includes both singular and plural of such term, unless clearly indicated within the claim otherwise (i.e., that the reference "a" or "an" clearly indicates only the singular or only the plural). Also, as used in the description herein and throughout the claims that follow, the meaning of "in" includes "in" and "on" unless the context clearly dictates otherwise. The scope of this disclosure should be determined by the following claims and their legal equivalents.

What is claimed is:

1. A method, comprising:

receiving, by a clinical documentation improvement (CDI) system executing on a processor, real time medical data for a population of a hospital or healthcare facility streamed from one or more hospital data sources;

translating, by the CDI system, the real time medical data to structured data for the hospital population, the structure data including tables, each table associated with a data type;

generating, by the CDI system, a medical alert using the tables;

determining, by the CDI system from the medical alert, a change to a first patient case of a plurality of patient cases associated with a first patient of a plurality of patients in the hospital population, the change associated with a location of the patient, a medical condition of the patient, a scheduled event to perform case evaluation, or a new indicator added to the first patient case;

accessing, by the CDI system, the plurality of patient cases for the hospital population stored in a database;

evaluating, by the CDI system, each of the plurality of patient cases, the evaluating including:
  resolving a Diagnosis-Related Group (DRG) code from zero or more DRG codes associated with each patient case, the resolving including determining, by the CDI system, whether a visit identifier from each patient case is associated with a final DRG code, a working DRG code, or an admitting DRG code, the visitor identifier associated with the patient's current stay at the hospital or healthcare facility; and
  determining a CDI scoring approach for the each patient case based at least in part on a result from the resolving;
generating, by the CDI system, a CDI score using the CDI scoring approach thus determined by the CDI system for the each patient case, the generating including:
  determining a first score;
  determining one or more factors that affect the each patient case;
  determining one or more adjustments based on the one or more factors; and
  applying the one or more adjustments to the first score, the applying producing an adjusted score;
converting, by the CDI system, the adjusted score into a final CDI score in a pre-defined range, the final CDI score representing a significance or level of improvement over clinical documentation about each patient case;
updating, by the CDI system, each patient case stored in the database to include the final CDI score; and
presenting the final CDI scores for multiple ones of the plurality of patient cases on a user interface running on a computing device communicatively connected to the CDI system, wherein the patient cases are prioritized according to the corresponding final CDI scores.

2. The method according to claim 1, wherein the one or more factors comprise a primary condition of the patient, a severity of the primary condition, a secondary condition that exacerbates the primary condition of the patient, a historical documentation performance measure associated with a hospital or a physician for the patient, a payer that reimburses the hospital or the physician for the patient, a hospital location for the patient, novelty of the change to the first patient case or temporal proximity to discharge of the patient.

3. The method according to claim 1, wherein the new indicator comprises a base DRG alert generated by an alert engine of the CDI system.

4. The method according to claim 1, further comprising:
performing the evaluating the first patient case responsive to the scheduled event.

5. The method according to claim 1, wherein if the CDI system is unable to resolve a DRG code from zero or more DRG codes associated with the first patient case, the CDI system generates the first score using an indicator weight of the new indicator or prompts a user to assign or select a working DRG code for the first patient case.

6. The method according to claim 1, further comprising:
if no DRG code is associated with the first patient case, determining an International Classification of Diseases (ICD) code associated with the first patient case and using the ICD code to find a DRG code for the first patient case.

7. The method according to claim 1, wherein the one or more adjustments include at least one of a length of stay adjustment, a documentation accuracy adjustment, a payer adjustment, a patient location adjustment, a documentation novelty adjustment, a review timing adjustment, a case size adjustment, or a documentation sufficiency adjustment.

8. The method according to claim 1, wherein the CDI scoring approach thus determined by the CDI system for the first patient case utilizes the DRG code from the resolving, a DRG probability, or an indicator weight of the new indicator in determining the first score.

9. The method according to claim 1, further comprising:
receiving, by the CDI system, user action via the user interface running on the computing device; and
re-evaluating, by the CDI system, the first patient case responsive to the user action received by the CDI system via the user interface running on the computing device; and
updating, by the CDI system, a display presented on the user interface to indicate a revised CDI score generated by the re-evaluating, wherein if the user action comprises marking the first patient case as reviewed, updating the display comprises removing the first patient case from the display for a predetermined interval.

10. The method according to claim 1, wherein the final CDI score for the first patient case is presented on the user interface in a sorted order with at least one other CDI score for another patient case associated with another patient in the hospital population, the sorted order prioritizing the presented patient cases according to the significance or level of improvement for clinical documentation associated with the presented patient cases.

11. A clinical documentation improvement (CDI) system, comprising:
at least one processor;
at least one non-transitory computer readable medium; and
stored instructions translatable by the at least one processor to perform:
  receiving real time medical data for a population of a hospital or healthcare facility streamed from one or more hospital data sources;
  translating the real time medical data to structured data, the structure data for the hospital population including tables, each table associated with a data type;
  generating a medical alert using the tables;
  determining, from the medical alert, a change to a first patient case of a plurality of patient cases associated with a first patient of a plurality of patients in the hospital population, the change associated with a location of the patient, a medical condition of the patient, a scheduled event to perform case evaluation, or a new indicator added to the first patient case;
  accessing the plurality of patient cases for the hospital population stored in a database;
  evaluating each of the plurality of patient cases, the evaluating including:
    resolving a Diagnosis-Related Group (DRG) code from zero or more DRG codes associated with each patient case, the resolving including determining whether a visit identifier from each patient case is associated with a final DRG code, a working DRG code, or an admitting DRG code, the visitor identifier associated with the patient's current stay at a hospital or healthcare facility; and
    determining a CDI scoring approach for each patient case based at least in part on a result from the resolving;
  generating a CDI score using the CDI scoring approach thus determined for each patient case, the generating including:

determining a first score;
determining one or more factors that affect each patient case;
determining one or more adjustments based on the one or more factors; and
applying the one or more adjustments to the first score, the applying producing an adjusted score;
converting the adjusted score into a final CDI score in a pre-defined range, the final CDI score representing a significance or level of improvement over clinical documentation about each patient case;
updating the patient case stored in the database to include the final CDI score; and
presenting the final CDI scores for multiple ones of the plurality of patient cases on a user interface running on a computing device communicatively connected to the CDI system, wherein the patient cases are prioritized according to the corresponding final CDI scores.

12. The CDI system of claim 11, wherein the one or more factors comprise a primary condition of the patient, a severity of the primary condition, a secondary condition that exacerbates the primary condition of the patient, a historical documentation performance measure associated with a hospital or a physician for the patient, a payer that reimburses the hospital or the physician for the patient, a hospital location for the patient, novelty of the change to the first patient case or temporal proximity to discharge of the patient.

13. The CDI system of claim 11, wherein the new indicator comprises a base DRG alert generated by an alert engine of the CDI system.

14. The CDI system of claim 11, wherein the stored instructions are further translatable by the at least one processor to perform the evaluating the first patient case responsive to the scheduled event.

15. The CDI system of claim 11, wherein if the CDI system is unable to resolve a DRG code from zero or more DRG codes associated with the first patient case, the CDI system generates the first score using an indicator weight of the new indicator or prompts a user to assign or select a working DRG code for the first patient case.

16. The CDI system of claim 11, wherein, if no DRG code is associated with the first patient case, the CDI system determines an International Classification of Diseases (ICD) code associated with the first patient case and uses the ICD code to find a DRG code for the first patient case.

17. The CDI system of claim 11, wherein the one or more adjustments include at least one of a length of stay adjustment, a documentation accuracy adjustment, a payer adjustment, a patient location adjustment, a documentation novelty adjustment, a review timing adjustment, a case size adjustment, or a documentation sufficiency adjustment.

18. The CDI system of claim 11, wherein the CDI scoring approach thus determined for the first patient case utilizes the DRG code from the resolving, a DRG probability, or an indicator weight of the new indicator in determining the first score.

19. The CDI system of claim 11, further comprising:
receiving user action via the user interface running on the computing device; and
re-evaluating the first patient case responsive to the user action received via the user interface running on the computing device; and
updating a display presented on the user interface to indicate a revised CDI score generated by the re-evaluating, wherein if the user action comprises marking the first patient case as reviewed, updating the display comprises removing the first patient case from the display for a predetermined interval.

20. The CDI system of claim 11, wherein the final CDI score for the first patient case is presented on the user interface in a sorted order with at least one other CDI score for another patient case associated with another patient in the hospital population, the sorted order prioritizing the presented patient cases according to the significance or level of improvement for clinical documentation associated with the presented patient cases.

* * * * *